US009994347B2

(12) United States Patent
Yuyama et al.

(10) Patent No.: US 9,994,347 B2
(45) Date of Patent: Jun. 12, 2018

(54) MEDICINE INSPECTION DEVICE AND MEDICINE PACKAGING SYSTEM

(71) Applicant: YUYAMA MFG. CO., LTD., Toyonaka-shi, Osaka (JP)

(72) Inventors: Hiroyuki Yuyama, Toyonaka (JP); Hirokazu Amano, Toyonaka (JP); Hiromichi Tsuda, Toyonaka (JP); Dai Shimizube, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 212 days.

(21) Appl. No.: 14/769,268

(22) PCT Filed: Feb. 20, 2014

(86) PCT No.: PCT/JP2014/053981
§ 371 (c)(1),
(2) Date: Nov. 30, 2015

(87) PCT Pub. No.: WO2014/129526
PCT Pub. Date: Aug. 28, 2014

(65) Prior Publication Data
US 2016/0114925 A1    Apr. 28, 2016

(30) Foreign Application Priority Data

Feb. 20, 2013   (JP) ................................. 2013-030757

(51) Int. Cl.
*G06K 9/00* (2006.01)
*B65B 57/16* (2006.01)
(Continued)

(52) U.S. Cl.
CPC ................ *B65B 57/16* (2013.01); *B65B 1/04* (2013.01); *G06F 17/30268* (2013.01);
(Continued)

(58) Field of Classification Search
None
See application file for complete search history.

(56) References Cited

U.S. PATENT DOCUMENTS 7,805,217 B2 *  9/2010  Chudy ................ G06F 19/3462
                                                        700/230
9,116,887 B2 *  8/2015  Botten .................... G06F 17/30
(Continued)

FOREIGN PATENT DOCUMENTS

JP       2005-34191 A     2/2005
JP       2008-18230 A     1/2008
(Continued)

*Primary Examiner* — Hadi Akhavannik
(74) *Attorney, Agent, or Firm* — Masuvalley & Partners

(57) ABSTRACT

A system for individually packaging medicine is provided with a medicine inspection device that is capable of performing inspection of medicine that is individually packaged using a device for individually packaging medicine or the like. The control device of the medicine inspection device is provided with an inspection database in which images of medicine are stored as master images and is capable of carrying out an inspection task using image matching processing that involves an image acquired by imaging. The control is also capable of performing similarity determination for determining whether a medicine that is similar to a medicine that is packaged in an individual wrapper is present in the inspection database in a state in which the reference scope of the inspection database is restricted.

13 Claims, 14 Drawing Sheets

(51) Int. Cl.
  *G06T 7/00* (2017.01)
  *G06F 19/00* (2018.01)
  *B65B 1/04* (2006.01)
  *G06F 17/30* (2006.01)
  *G06K 9/46* (2006.01)
  *G06K 9/62* (2006.01)
  *G06T 7/11* (2017.01)

(52) U.S. Cl.
  CPC ........ *G06F 19/321* (2013.01); *G06F 19/3462* (2013.01); *G06K 9/46* (2013.01); *G06K 9/6215* (2013.01); *G06T 7/0004* (2013.01); *G06T 7/11* (2017.01); *G06T 2207/30108* (2013.01)

(56) References Cited

U.S. PATENT DOCUMENTS

| | | | |
|---|---|---|---|
| 2006/0088196 A1* | 4/2006 | Popovich, Jr. | G06T 7/001 382/128 |
| 2007/0185615 A1 | 8/2007 | Bossi et al. | |
| 2007/0189597 A1* | 8/2007 | Limer | A61J 7/02 382/153 |
| 2008/0056556 A1* | 3/2008 | Eller | G06F 19/327 382/142 |
| 2009/0080735 A1* | 3/2009 | Chapman | G06T 7/0004 382/128 |
| 2009/0299522 A1* | 12/2009 | Savir | A61J 7/0084 700/240 |
| 2010/0232640 A1* | 9/2010 | Friend | G06F 19/3462 382/100 |
| 2012/0084091 A1* | 4/2012 | Hanina | G06F 19/3456 705/2 |
| 2012/0163685 A1* | 6/2012 | Rothschild | G06F 19/3456 382/128 |
| 2012/0189177 A1* | 7/2012 | Oh | G06K 9/228 382/128 |
| 2013/0028480 A1* | 1/2013 | Rothschild | G06F 19/3456 382/103 |

FOREIGN PATENT DOCUMENTS

| | | |
|---|---|---|
| JP | 2010-165159 A | 7/2010 |
| JP | 2012-245032 A | 12/2012 |
| JP | 2013-17745 A | 1/2013 |
| WO | 2012/147907 A1 | 11/2012 |

\* cited by examiner

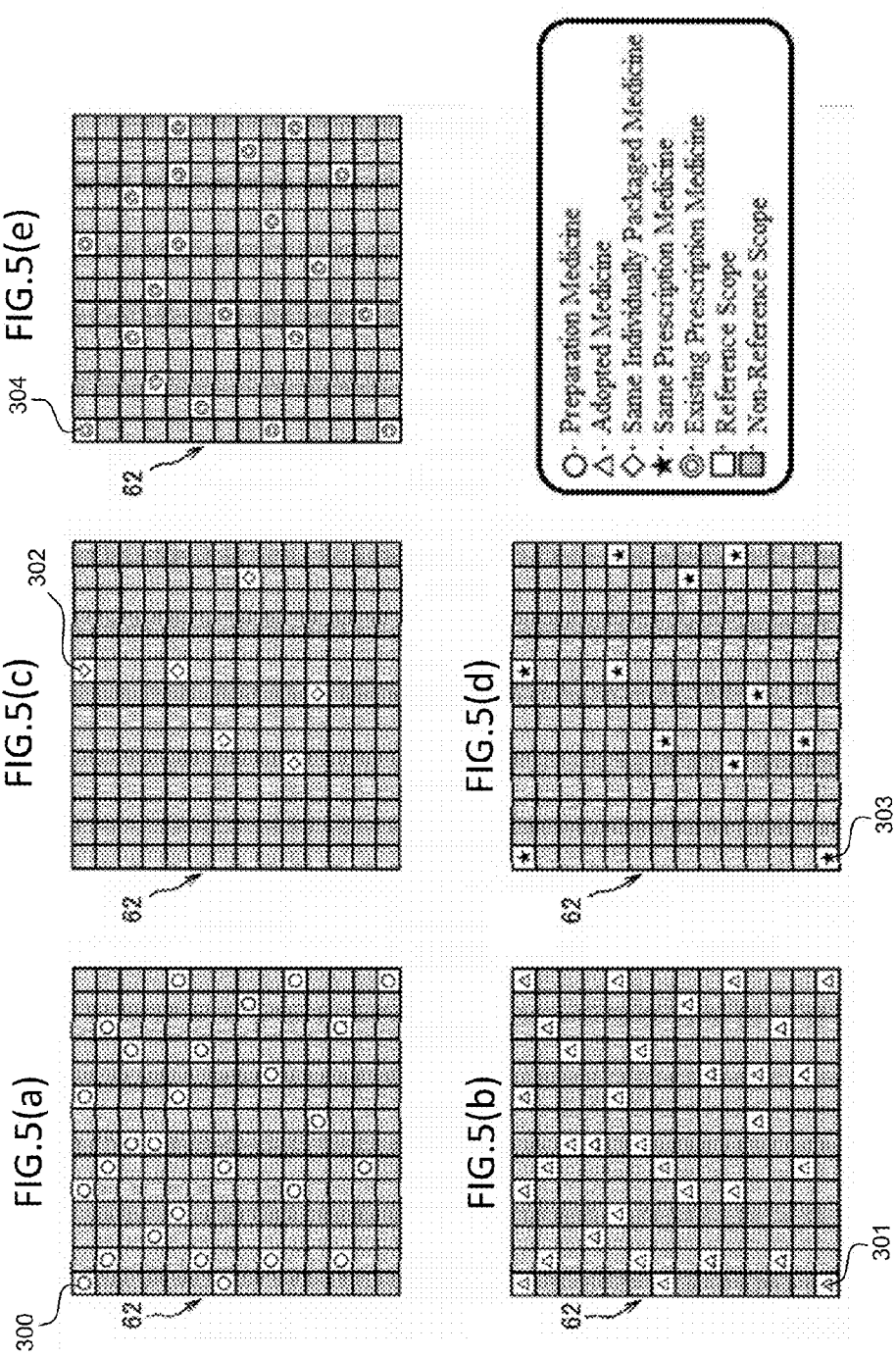

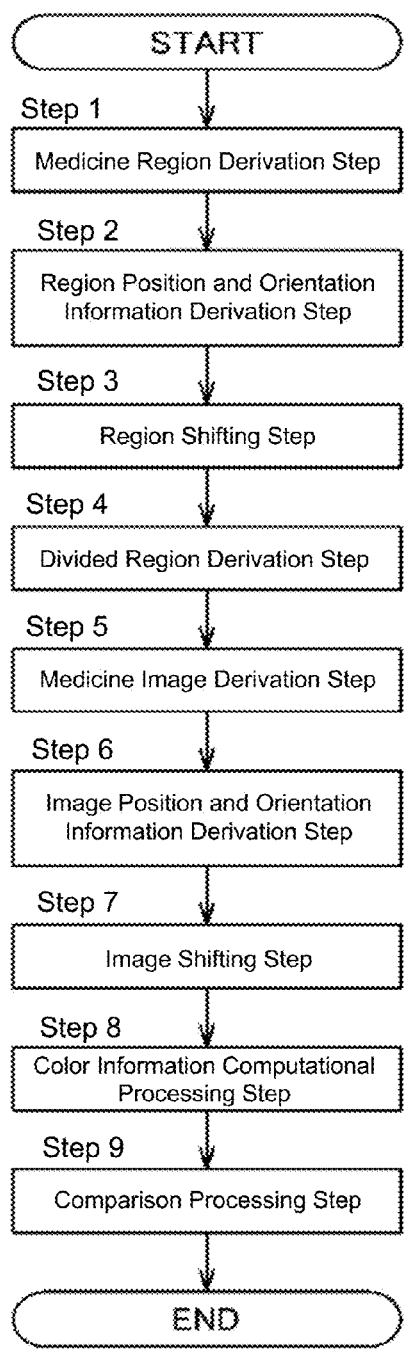

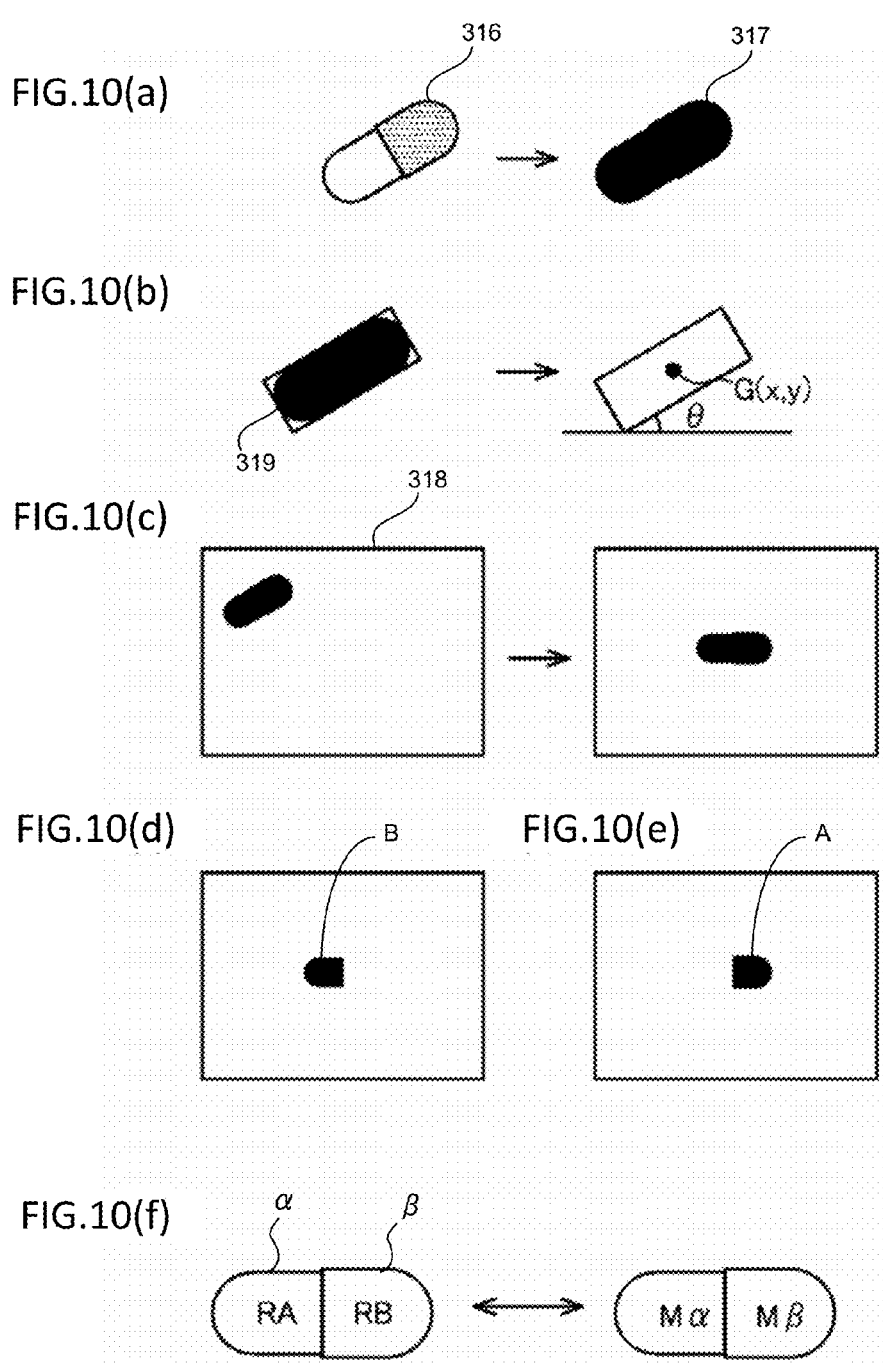

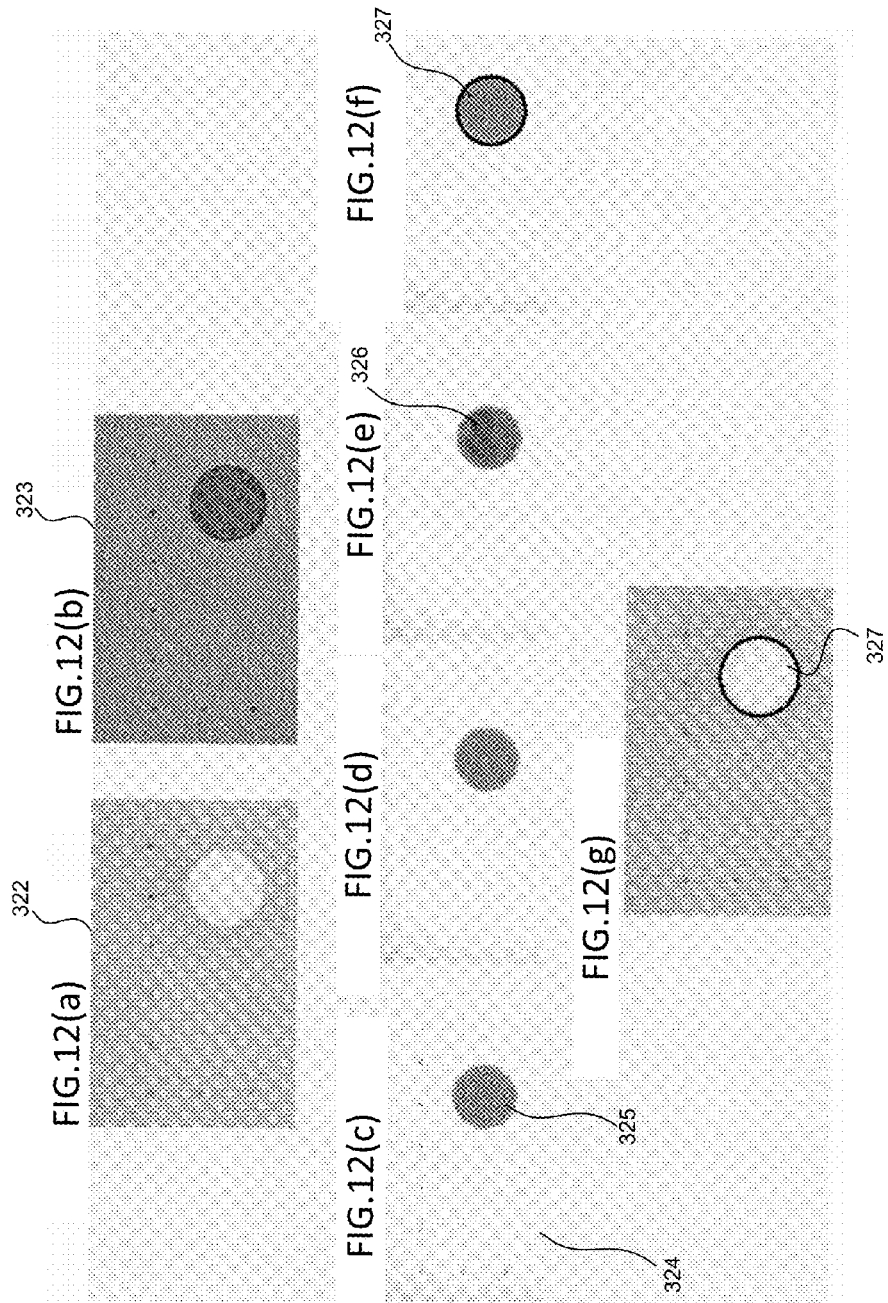

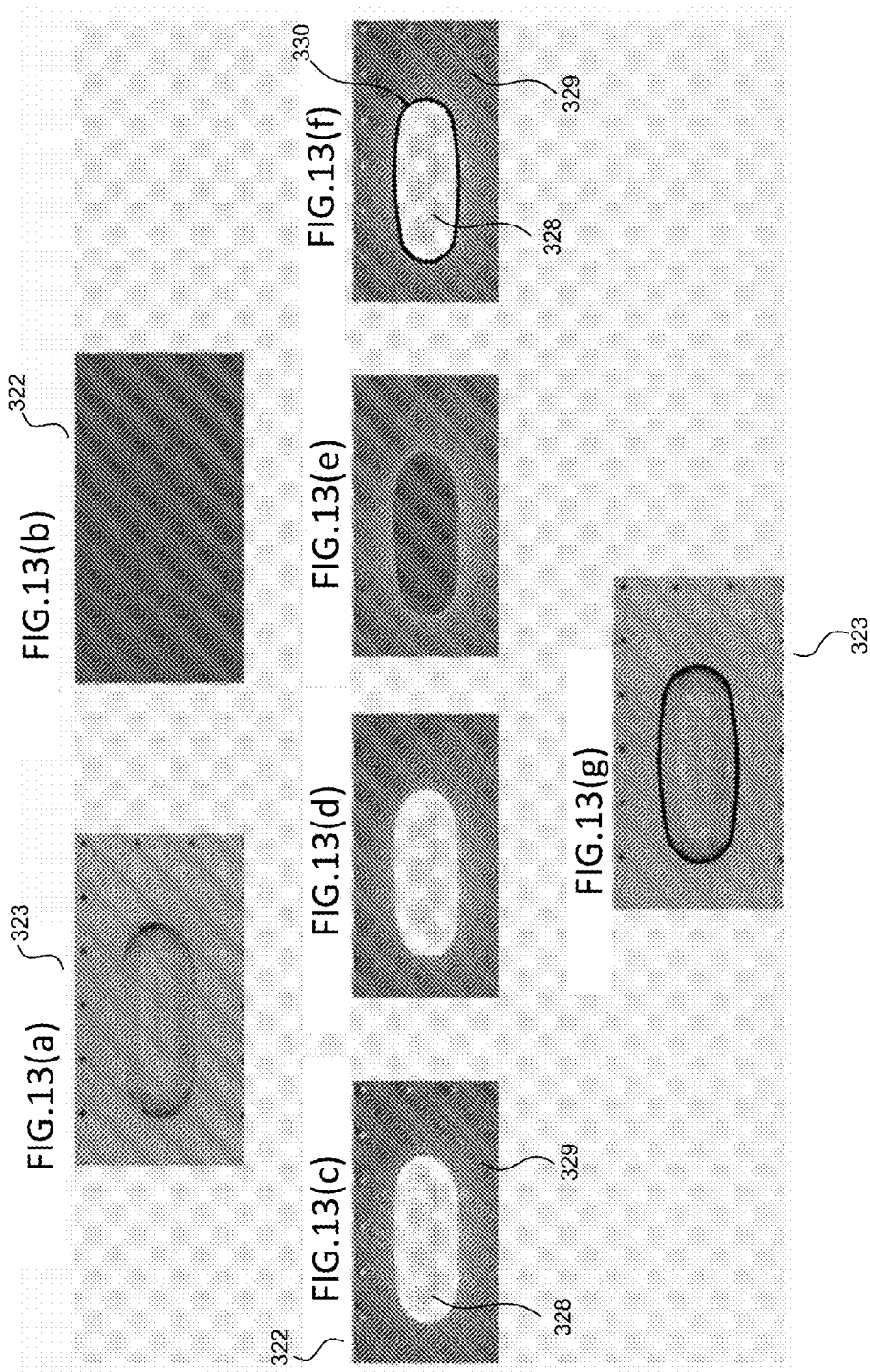

MEDICINE INSPECTION DEVICE AND MEDICINE PACKAGING SYSTEM

RELATED APPLICATIONS

This application is the U.S. National Phase of and claims priority to International Patent Application No. PCT/JP2014/053981, International Filing Date Feb. 20, 2014, entitled MEDICINE INSPECTION DEVICE AND SYSTEM FOR INDIVIDUALLY PACKAGING MEDICINE, which claims priority to, and benefit of, Japanese Application No. JP2013-030757, filed Feb. 20, 2013, all of which are incorporated herein by reference in their entireties.

TECHNICAL FIELD

The present invention pertains to a medicine inspection device for inspecting whether or not a medicine has been divided and packaged according to a prescription, and a system for individually packaging medicine, the system thereof provided with the medicine inspection device and a medicine dividing and packaging device.

BACKGROUND

Conventionally a tablet inspection system like that disclosed by the following patent document 1 is provided. With the tablet inspection system disclosed by the following patent document 1, a solid medicine in the form of a granular substance, capsule, or the like can be divided in separate packaging paper in individual dosage portions and supplied. Moreover, the tablet inspection system according to the Japanese Unexamined Patent Application Publication No. H07-200770 is configured such that solid medicine in a state of being divided and packaged in separate packaging paper is photographed, and a numerical quantity of the solid medicine is inspected based on the image thereby obtained.

SUMMARY OF THE INVENTION

Problem to be Solved by the Invention

Here, the inventors of the present invention developed a prototype medicine inspection device for inspecting a medicine packaged in a divided packaging bag based on an image photographed of that medicine, the device thereof being provided with an inspection database which gathers information about the medicine that needs to be inspected, and being capable of implementing an inspection (medicine type comparison inspection, quantity comparison inspection) to inspect whether or not a medicine divided and packaged in a divided packaging bag is divided and packaged with the correct medicine type and quantity according to a prescription by referencing the inspection database, and in addition to determining whether a type of medicine has been divided and packaged according to a prescription by implementing a medicine type comparison inspection, the medicine inspection device is also capable of determining whether a medicine similar to the divided and packaged medicine is present in the medicine registered in the inspection database (similarity determination), and of drawing attention to a similar medicine. As a result, even if an inspection result is obtained that indicates that the medicine type and quantity are in accordance with the prescription and that there are no problems, numerous medicines are extracted as similar medicines through the similarity determination, and thus it was determined that confirmation through a visual inspection or the like by the pharmacist or other user is required, and that the tasks could possibly become more cumbersome by that confirmation portion alone.

Based on that knowledge, the inventors of the present invention conducted further diligent examinations, and as a result, gained further knowledge that even if a medicine determined to be similar through a similarity determination is a medicine for which erroneous dividing and packaging cannot occur because of a reason such as, for example, it is not used in divided packaging, an alarm or the like is generated to indicate that gist. In other words, the inventors of the present invention gained the knowledge that by referencing data for all medicine registered in the inspection database when implementing a similarity determination, in addition to inspecting to determine if a medicine has been divided and packaged in accordance with a prescription, all possible measures can also be expended for the similarity determination, but alarms can be excessively generated for the presence of similar medicines, and this can lead to the operations becoming more cumbersome. Knowledge was also gained that when the reference scope of the inspection database in the similarity determination is set to include the entire range, the load required for similarity determination processing can potentially become immense.

Therefore, an object of the present invention is to provide a medicine inspection device that is capable of avoiding the excessive determination of the presence of similar medicines through a similarity determination which determines the presence of medicines similar to the medicine divided and packaged in the divided packaging bag and of minimizing the load required for similarity determination processing, and to provide a system for individually packaging medicine that is provided with the medicine inspection device.

Means for Solving the Problem

The present invention, which is provided to solve the above-described problem, is a medicine inspection device for inspecting whether or not a medicine has been divided and packaged according to a prescription in a divided packaging bag formed by dividing and packaging the medicine into single packages based on the prescription using a medicine dividing and packaging device, and the medicine inspection device includes: an inspection database in which information regarding medicines necessary for implementing an inspection is accumulated; and a control device capable of implementing similarity determination by referencing the inspection database and outputting the presence of a medicine similar to the medicine divided and packaged in the divided packaging bag as a determination result; wherein, the control device is capable of implementing similarity determination through a preparation medicine limiting mode, which limits the reference scope of the inspection database to within a scope of medicines registered as medicines to be packaged by the medicine dividing and packaging device With the medicine inspection device of the present invention, similarity determination can be implemented with the reference scope of the inspection database limited to within a scope of medicines registered as medicines to be packaged by the medicine dividing and packaging device by selecting the preparation medicine limiting mode as the mode for implementing the similarity determination. Through this, medicines that have not been prepared for dividing and packaging at the pharmacy or the like where the medicine dividing and packaging device is installed and for which the possibility of erroneous dividing and packaging is assumed to be very low can be removed from the target of similarity determination, and the problem of excessively determining the presence of similar medicines through similarity determination can be resolved. Moreover, the processing load required for similarity determination can be reduced, the processing speed thereof can be improved, and convenience can be further improved. Note that in the description of the present invention and this specification, the phrase "medicines registered as medicines to be packaged" is a concept that includes medicines to be divided and packaged by a medicine dividing and packaging device, and insofar as a medicine that is registered as a medicine to be packaged, the phrase also includes medicines that cannot be packaged by a dividing and packaging machine but are prepared in separate cassettes or the like for a medicine dividing and packaging device, medicines requiring cold storage and prepared using a cassette or the like in preparation for packaging by a medicine dividing and packaging device, and medicines which are not packaged but are used in dividing and packaging such as medicines manually supplied to a medicine dividing and packaging device for use in dividing and packaging, and the like.

Moreover, the present invention is a medicine inspection device for inspecting whether or not a medicine has been divided and packaged according to a prescription in a divided packaging bag formed by dividing and packaging the medicine into single packages based on the prescription using a medicine dividing and packaging device; and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, the control device is capable of implementing similarity determination through an adopted medicine limiting mode, which limits the reference scope of the inspection database to within a scope of medicines registered as medicines to be prepared for dividing and packaging from amongst medicines registered in the inspection database.

With the medicine inspection device of the present invention, a similarity determination can be implemented with the reference scope of the inspection database limited to within a scope of medicines registered as medicines prepared for dividing and packaging by selecting the adopted medicine limiting mode as the implementation mode for similarity determination. Through this, medicines which are not adopted for dividing and packaging and for which the possibility of erroneous dividing and packaging is extremely low are excluded from the target for similarity determination, and contributions can be made to reducing the excessive generation of determinations of the presence of similar medicines through similarity determination, reducing the similarity determination load, and improving the processing speed. Here, the phrase "medicines registered as medicines prepared for dividing and packaging" in the present invention is a concept that includes not only medicines packaged and prepared for dividing and packaging using a medicine dividing and packaging device, but also for example, medicines actually packaged or prepared for packaging using a medicine dividing and packaging device, as well as all medicines adopted for dividing and packaging within a pharmacy or other facility or within a pharmacy chain.

The present invention is a medicine inspection device for inspecting whether or not a medicine has been divided and packaged according to a prescription in a divided packaging bag formed by dividing and packaging the medicine into single packages based on the prescription, and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, the control device is capable of implementing similarity determination through an identical divided and packaged medicine limiting mode, which limits the reference scope of the inspection database to within a scope of medicines contained within a divided packaging bag.

With the medicine inspection device of the present invention, the similarity determination can be implemented with the identical divided and packaged medicine limiting mode, which limits the reference scope of the inspection database to within a scope of medicines contained within a divided packaging bag. Through this, the reference scope of the inspection database can be significantly narrowed down, where the excessive determination of the presence of similar medicines can be avoided, and contributions can be made to accelerating the overall inspection operation.

The present invention is a medicine inspection device for inspecting whether or not a medicine has been divided and packaged according to a prescription in a divided packaging bag formed by dividing and packaging the medicine into single packages based on the prescription, and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, the control device is capable of implementing similarity determination through an identical prescription medicine limiting mode, which limits the reference scope of the inspection database to within a scope of medicines used in prescriptions of a same patient.

With the medicine inspection device of the present invention, when the identical prescription medicine limiting mode is selected as the mode for implementing similarity determination, the reference scope of the inspection database is limited to within a scope of medicines used in prescriptions of the same patient. By limiting the reference scope of the inspection database in this manner, the excessive determination of the presence of similar medicines through similarity determination can be avoided, and the overall inspection operation can be accelerated.

Moreover, a medicine inspection device of the present invention is a device for inspecting whether or not a medicine has been divided and packaged according to a prescription in a divided packaging bag formed by dividing and packaging the medicine into single packages based on the prescription, and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, the control device is capable of implementing similarity determination through a prescription history limiting mode, which limits the reference scope of the inspection database to within a scope of medicines having a history of being prescribed for the patient corresponding to the divided packaging bag that is the target of inspection.

With the medicine inspection device of the present invention, the reference scope of the inspection database when implementing similarity determination can be significantly limited by selecting the prescription history limiting mode. Moreover, if the prescription history limiting mode is selected, a similarity determination can be implemented with consideration of the medicine prescription history of the given patient. Therefore, according to the medicine inspection device of the present invention, similarity determination can be smoothly and efficiently implemented with consideration of the prescription history.

A medicine inspection device of the present invention is a device for inspecting whether or not a medicine has been divided and packaged according to a prescription in a divided packaging bag formed by dividing and packaging the medicine into single packages based on the prescription using a medicine dividing and packaging device, and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, a determination level uniformizing mode, which implements similarity determination using a reference scope of the inspection database as a same scope for all single divided packaging bag groups divided and packaged based on a same prescription, and a determination level weighting mode can be selected, where the reference scope of the inspection database for similarity determination is dissimilated between during the inspection of a divided packaging bag, which makes up a portion of the divided packaging bag group, and during the inspection of other divided packaging bags; and conditional upon the medicine dividing and packaging device having a manual medicine supply unit capable of dispersing and inserting medicines in single package portions at a time, and capable of supplying single package portions at a time as portions for dividing and packaging, by selecting the determination level weighting mode, similarity determination can be implemented such that the reference scope of the inspection database referenced for similarity determination regarding a divided packaging bag in which medicines prepared by the manual medicine supply unit are packaged, is a broader scope than the reference scope of the inspection database referenced for similarity determination regarding other divided packaging bags.

With the medicine inspection device of the present invention, the reference scope of the inspection database can be selected by selecting either the determination level uniformizing mode or the determination level weighting mode when performing similarity determination of a divided packaging bag in which medicine supplied from the manual medicine supply unit has been divided and packaged. In other words, by selecting the determination level weighting mode, the reference scope of the inspection database that is the target for similarity determination regarding divided packaging bags in which medicine supplied from a manual medicine supply unit are divided and packaged is expanded compared to when the determination level uniformizing mode is selected. Through this, a similarity determination can be implemented with weighting applied for divided packaging bags containing medicine prepared by the manual medicine supply unit through manual dispersing, which requires attention during inspection.

A medicine inspection device of the present invention is a medicine inspection device for inspecting whether or not a medicine has been divided and packaged according to a prescription in a divided packaging bag formed by dividing and packaging the medicine into single packages based on the prescription using a medicine dividing and packaging device, and the medicine inspection device includes an inspection database in which information regarding medicines necessary for implementing an inspection is accumulated; and a control device capable of implementing similarity determination by referencing the inspection database and outputting the presence of a medicine similar to a medicine divided and packaged in the divided packaging bag as a determination result; wherein, a determination level uniformizing mode, which implements similarity determination using a reference scope of the inspection database as a same scope for all single divided packaging bag groups divided and packaged based on a same prescription, and a determination level weighting mode can be selected, where the reference scope of the inspection database for similarity determination is dissimilated between during the inspection of a divided packaging bag, which makes up a portion of the divided packaging bag group, and during the inspection of other divided packaging bags; and by selecting the determination level weighting mode, similarity determination can be implemented such that the reference scope of the inspection database referenced in the similarity determination regarding a divided packaging bag in which medicines registered as medicines requiring caution (medicines requiring control) from amongst medicines registered in the inspection database is a broader scope than the reference scope of the inspection database referenced in a similarity determination regarding other divided packaging bags.

With the medicine inspection device of the present invention, in addition to the determination level uniformizing mode, a determination level weighting mode is provided, and by selecting the determination level weighting mode, similarity determination can be implemented with weighting applied to the determination level for a portion of a divided packaging bag group, which is of the same prescription. More specifically, by selecting the determination level weighting mode, if similarity determination is implemented for a divided packaging bag in which medicine registered as a medicine requiring caution is packaged, the reference scope of the inspection database can be expanded compared to when similarity determination is performed for other divided packaging bags. Through this, similarity determination can be implemented with weighting applied to divided packaging bags containing medicines that require caution in the inspection process.

The above-described medicine inspection devices of the present invention may also be capable of implementing a medicine type comparison inspection, which implements a comparison including a similarity determination regarding whether or not the medicine type of the medicine divided and packaged in the divided packaging bag matches the prescription, and a quantity comparison inspection, which determines whether or not the quantity of the medicine is in accordance with the prescription; and may be capable of selectively implementing a full comparison mode, which implements both the medicine type comparison inspection and the quantity comparison inspection, and a quantity comparison limited mode, which implements the quantity comparison inspection without implementing the medicine type comparison inspection.

With the medicine inspection device of the present invention, by selecting the full comparison mode, both the medicine type comparison inspection, which includes the similarity determination, and the quantity comparison inspection can be implemented, and the inspection precision can be improved. Moreover, by selecting the quantity comparison limited mode with the medicine inspection device of the present invention, the quantity comparison inspection can be implemented while omitting the medicine type comparison inspection, which includes the similarity determination, and an excessive determination of the presence of similar medicines through the inspection operation can be avoided. Therefore, with the medicine inspection device of the present invention, the appropriate operation mode can be selected according to whether similarity determination is required.

The above-described medicine inspection devices may also be capable of implementing an inspection to determine whether or not a medicine that is divided and packaged matches a prescription based on color information obtained from a photographed image of the medicine that is the target of inspection; wherein the medicine inspection device includes a database in which color information of medicines is recorded, and an inspection can be implemented to determine whether or not a medicine targeted for inspection is a medicine compared in the database by comparing color information of the medicine obtained from the photographed imaged and color information of each medicine registered in the database; and regarding long medicines having a long shape in a prescribed direction and for which the color is different with a center part in the longitudinal direction as a boundary, color information for one side of the boundary and color information for the other side of the boundary are recorded respectively as master data (M$\alpha$, M$\beta$) in the database; color information for a region on one side (RA) of a long medicine and color information for a region on the other side (RB) thereof with a center part in the longitudinal direction as a boundary are respectively derived from an image of a long medicine in a photographed image; and if a combination of the color information (RA, RB) matches a combination of the master data (M$\alpha$, M$\beta$) for a long medicine compared in the database, a determination is made that the medicine thereof is the long medicine to which it was compared.

According to the medicine inspection device of the present invention, the inspection precision of a long medicine, for which colors differ with a center part in the longitudinal direction as a boundary, such as with so-called capsule agents and caplet agents modelled after capsule agents, can be improved. Moreover, the excessive determination of the presence of a medicine similar to the medicine targeted for inspection can be avoided, and the overall inspection operation can be accelerated.

Moreover, a medicine inspection device of the present invention is a medicine inspection device for inspecting whether or not a medicine has been divided and packaged according to a prescription in a divided packaging bag formed by dividing and packaging the medicine into single packages based on the prescription using a medicine dividing and packaging device, and the medicine inspection device includes a conveying means for conveying a continuous divided packaging bag body having divided packaging bags formed continuously via a boundary; an inspection unit at which divided packaging bags that are the target of inspection are arranged; a photographing device for photographing a divided packaging bag arranged at the inspection unit through conveyance by the conveying means; an inspection database in which information regarding medicines including master images pertaining to the exterior shapes of medicines is accumulated; a medicine inspection processing capable of implementing image matching processing to match a master image registered in the inspection database and an image obtained by the photographing device, to inspect whether or not a medicine has been packaged in accordance with a prescription in a divided packaging bag; and a control device that is capable of implementing a supply control to convey and supply the continuous divided packaging bag body by the conveying means; wherein a divided packaging bag targeted for inspection is supplied to the inspection unit by the supply control, and if both a boundary on the upstream side and a boundary on the downstream side in the conveyance direction with respect to the divided packaging bag that has arrived at the inspection unit are contained in an image photographed by the photographing device, it may be determined by the control device that the divided packaging bag that is the target for inspection has been positioned with good precision with respect to the inspection unit; and if only one of either the boundary on the upstream side or the boundary on the downstream side in the conveyance direction with respect to the divided packaging bag that has arrived at the inspection unit is contained in the image, it may be determined by the control device that the divided packaging bag is in a state of being positionally deviated with respect to the inspection unit.

With the medicine inspection device of the present invention, the presence of positional deviation of a divided packaging bag with respect to the inspection unit can be determined using an image photographed by the photographing device of the divided packaging bag conveyed to the inspection unit by the supply control, and based on how a boundary formed between adjoining divided packaging bags is contained in the image. In this manner, operations can be performed by the medicine inspection device of the present invention with consideration of positional deviation of the divided packaging bag with respect to the inspection unit. More specifically, if positional deviation of the divided packaging bag can be understood as with the present invention, an operation can be performed to correct any positional deviation of a divided packaging bag when it occurs, an alarm can be generated when positional deviation occurs, and the like, and therefore contributions can be made to improving inspection precision.

Moreover, the above-described medicine inspection device of the present invention is preferably a medicine inspection device wherein if only the boundary on the upstream side in the conveyance direction with respect to the divided packaging bag that has arrived at the inspection unit is contained in the image, the control device determines that the divided packaging bag is in a state of being positionally deviated at the downstream side with respect to the inspection unit; and if only the boundary on the downstream side in the conveyance direction with respect to the divided packaging bag that has arrived at the inspection unit is contained in the image, the control device determines that the divided packaging bag is in a state of being positionally deviated at the upstream side with respect to the inspection unit.

By adopting the configuration thereof, even if a positional deviation of the divided packaging bag with respect to the inspection unit occurs, the device is capable of accurately determining whether the deviation direction is at the upstream side or the downstream side in the conveyance direction of the continuous divided packaging bag body.

The medicine inspection device of the present invention is a medicine inspection device for inspecting whether or not a medicine has been divided and packaged according to a prescription in a divided packaging bag formed by dividing and packaging the medicine into single packages based on the prescription using a medicine dividing and packaging device, and the medicine inspection device includes an inspection unit at which divided packaging bags that are the target of inspection are arranged; a photographing device for photographing a divided packaging bag arranged at the inspection unit through conveyance by the conveying means; an inspection database in which information regarding medicines including master images pertaining to the exterior shapes of medicines is accumulated; and a control device capable of implementing image matching processing to match a master image registered in the inspection database and an image obtained by the photographing device, and of implementing medicine inspection processing to inspect whether or not a medicine has been packaged in accordance with a prescription in a divided packaging bag; and the medicine inspection device is capable of implementing a master image acquisition operation to acquire the master image pertaining to the medicine based on images of medicines acquired by the photographing device; wherein with the master image acquisition operation, a step of acquiring a front side image obtained by using the photographing device to photograph a divided packaging bag arranged at the inspection unit and a medicine arranged at the inspection unit; a step of acquiring an image for which the chroma component of the front side image has been extracted; a step of deriving a high brightness region which has a higher level of brightness than a prescribed brightness in the image for which the chroma component has been extracted; a step of deriving a contour of the high brightness region; and a step of acquiring an image within a region corresponding to a region enclosed by the contour in the front side image as a master image can be executed.

With the medicine inspection device of the present invention, an image for which the chroma component has been extracted from the front side image obtained by photographing medicine arranged at the inspection unit can be obtained by executing the master image acquisition operation. Furthermore, by deriving a contour of a high brightness region contained in an image for which the chroma component has been extracted, the region where the medicine has been photographed in the front side image can be specified. With the medicine inspection device of the present invention, an image in a region corresponding to the region enclosed by the above-described contour in the front side image is acquired as a master image of each medicine. Therefore, even if the medicine is a translucent medicine, a master image can be accurately obtained by obtaining the master image of each medicine in this manner.

A system for individually packaging medicine of the present invention is provided with an above-described medicine inspection device of the present invention, and a medicine dividing and packaging device capable of dividing and packaging a medicine into divided packaging bags in single package portions in accordance with a prescription; wherein medicines that have been divided and packaged at the medicine dividing and packaging device can be inspected by the medicine inspection device.

According to the configuration thereof, similarity determination for a medicine packaged in a divided packaging bag divided and packaged by the medicine dividing and packaging device can be more smoothly executed.

Effect of the Invention

According to the present invention, a medicine inspection device capable of more smoothly executing similarity determination to determine the presence of a medicine similar to a medicine divided and packaged in a divided packaging bag, and a system for individually packaging medicine provided with the medicine inspection device can be provided.

BRIEF DESCRIPTION OF THE DRAWINGS

FIG. 5(a) to FIG. 5(e) are an explanatory diagram conceptually showing a reference scope of the inspection database during similarity determination, FIG. 5(a) shows conditions during the preparation medicine limiting mode, FIG. 5(b) shows conditions during the adopted medicine limiting mode, FIG. 5 (c) shows conditions during the identical divided and packaged medicine limiting mode, FIG. 5 (d) shows during the identical prescription medicine limiting mode, and FIG. 5 (e) shows conditions during the prescription history limiting mode.

FIG. 9 is a flow chart pertaining to dichromic determination processing.

FIG. 10(a) to FIG. 10(f) are an explanatory diagram schematically showing an image used in dichromic determination processing.

FIG. 11(a) shows a correctly positioned state, and FIG. 11(b) and FIG. 11(c) show states of being positionally deviated in the conveyance direction.

FIG. 12(a) to FIG. 12(g) are an image diagram showing images obtained when a contour for a non-translucent medicine is derived.

FIG. 13(a) to FIG. 12(g) are an image diagram showing images obtained when a contour for a translucent medicine is derived.

MODE FOR CARRYING OUT THE INVENTION

Figure 1:
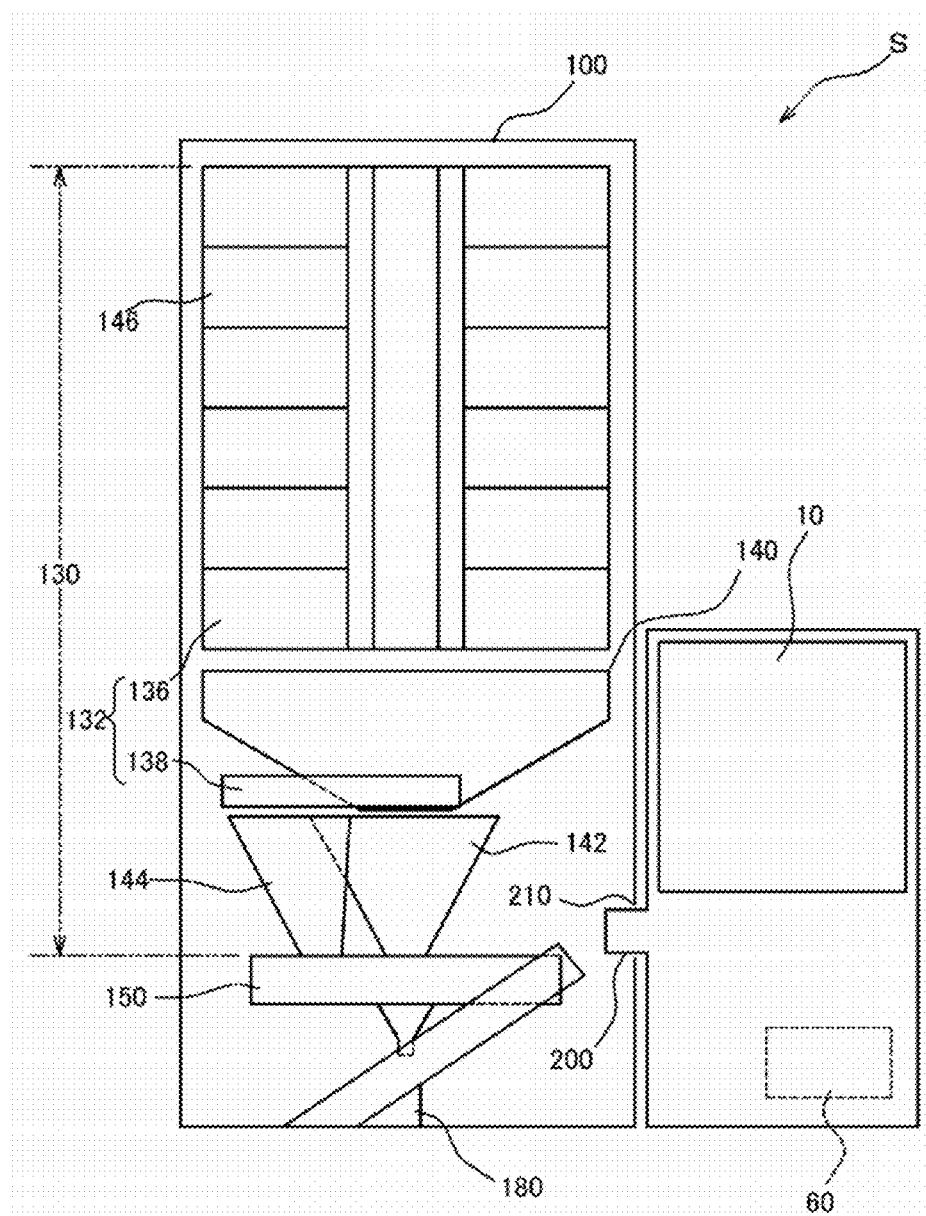
FIG. 1 is an explanatory diagram showing an outline configuration of the system for individually packaging medicine of the present invention.

A system S for individually packaging medicine and a medicine inspection device 10 according to an embodiment of the present invention are described in detail below with reference to the drawings. As shown in FIG. 1, the system S for individually packaging medicine is provided with the medicine inspection device 10 and a medicine dividing and packaging device 100.

The system S for individually packaging medicine may be driven with the medicine inspection device 10 and the medicine dividing and packaging device 100 interlocked, or may be driven with the medicine inspection device 10 and the medicine dividing and packaging device 100 independent from each other. In other words, the medicine dividing and packaging device S can execute operations to supply a divided packaging bag that has been divided and packaged by the medicine dividing and packaging device 100 as is to the medicine inspection device 10 for inspection. Moreover, a divided packaging bag that has been divided and packaged by the medicine dividing and packaging device 100 or another dividing and packaging device can be inspected by the medicine inspection device 10, or only dividing and packaging of the medicine can be implemented by the medicine dividing and packaging device 100 without operating the medicine inspection device 10. Furthermore, the system S for individually packaging medicine may also be configured with a separately provided winding and feeding device capable winding up and sequentially feeding out a continuous divided packaging bag body formed such that a plurality of divided packaging bags are continued in a strip shape. By configuring the system S for individually packaging medicine in this manner, a continuous divided packaging bag body prepared by the medicine dividing and packaging device 100 can be wound up by the winding and feeding device, and a sequentially fed continuous divided packaging bag body can be inspected by the medicine inspection device 10. The medicine inspection device 10 and the medicine dividing and packaging device 100 are described in further detail below.

<<Medicine Dividing and Packaging Device 100>>

The medicine dividing and packaging device 100 is a device that is capable of dividing and packaging medicine in accordance with prescription data that has been input, and then discharging the packaged medicine. A medicine supply means 130, a medicine preparation means 150, and a medicine packaging means 180 are provided within the main body of the medicine dividing and packaging device 100.

The medicine supply means 130 is provided to store solid medicine, appropriately discharge solid medicine in accordance with a prescription, and supply the medicine thereof to the medicine packaging means 180. The medicine supply means 130 is provided with a supply unit 132. The supply unit 132 stores solid medicine, and has a function of discharging solid medicine according to a prescription to the medicine preparation means 150. In addition, the medicine preparation means 150 functions to accumulate the solid medicine supplied from the supply unit 132 in single package portions, and to sequentially discharge the single package portions thereof to the medicine packaging means 180.

As means to supply solid medicine, the supply unit 132 has a feeder type supply unit 136 and a manual medicine supply unit 138. In addition, the supply unit 132 is provided with a standby hopper 140, a collection hopper 142, a manual dispersing hopper 144, and the like. The feeder type supply unit 136 is provided with a plurality of cassette type medicine feeders 146, and is capable of discharging solid medicine prepared for each medicine type in advance in each medicine feeder 146 in accordance with a prescription. The standby hopper 140 is arranged below the feeder type supply unit 136, and after the standby hopper 140 gathers single package portions of solid medicine fed from each medicine feeder 146, it is capable of discharging the single package portions thereof all at once. Solid medicine discharged from the standby hopper 140 is supplied in single package portions to the medicine preparation means 150 via the collection hopper 142 provided below the standby hopper 140.

Moreover, the manual medicine supply unit 138 is provided separately from the feeder type supply unit 136, and similar to the feeder type supply unit 136, is capable of supplying solid medicine to the medicine preparation means 150 side. A plurality of square shaped recesses are provided in the manual medicine supply unit 138 for dispersing and inserting medicine in single package portions, and medicine prepared in the recesses thereof can be supplied for dividing and packaging.

The medicine preparation means 150 is arranged further below than the above-described supply unit 132. The medicine preparation means 150 is capable of accumulating single package portions of solid medicine received from the medicine supply means 130 via the above-described collection hopper 142 and manual dispersing hopper 144, and of supplying the single package portions thereof to the medicine packaging means 180.

The medicine packaging means 180 is capable of forming each divided packaging bag by folding and adhering strip shaped separate packaging paper that has been prepared in advance, and of packaging single dose portions of medicine supplied from the medicine preparation means 150 side in the divided packaging bags. In this manner, a strip shaped continuous divided packaging bag body having a plurality of continuous divided packaging bags is formed. The continuous divided packaging bag body formed by the medicine packaging means 180 is discharged towards the medicine inspection device 10 from a discharge slot 200 provided at the main body of a medicine dividing and packaging unit 120.

Here, a connecting part 210 which can be connected to the discharge slot 200 of the medicine dividing and packaging unit 120 is provided at the medicine inspection device 10 side of the medicine dividing and packaging device 100, and the medicine inspection device 10 and the medicine dividing and packaging unit 120 are connected via this connecting part 210. Moreover, the configuration is such that the continuous divided packaging bag body discharged from the discharge slot 200 can be introduced into the medicine inspection device 10 via the connecting part 210, and can be supplied to the medicine inspection device 10. Therefore, with the system S for individually packaging medicine, when a continuous divided packaging body is formed by the medicine packaging means 180, next, an inspection of medicine contained in each divided packaging bag configuring the continuous divided packaging bag body thereof can be continuously implemented by the medicine inspection device 10, which will be described in detail below. Moreover, as described above, if a winding and feeding device is separately provided, an inspection can be continuously implemented by using the winding and feeding device to wind up the continuous divided packaging bag body prepared by the medicine dividing and packaging device 100, and to sequentially feed out divided packaging bags (the continuous divided packaging bag body) in a manner that is tailored to the progress of the inspection at the medicine inspection device 10.

<<Medicine Inspection Device 10>>

Figure 2A:
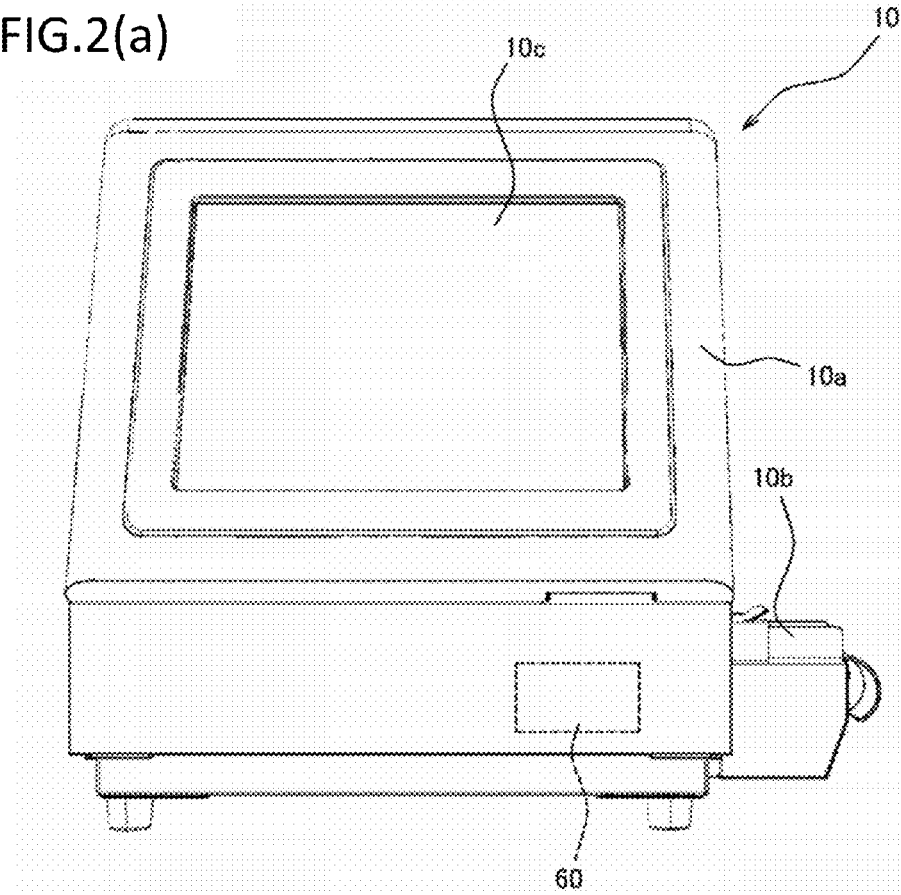
FIG. 2(a) is a front view of a medicine inspection device according to an embodiment of the present invention.
Figure 2B:
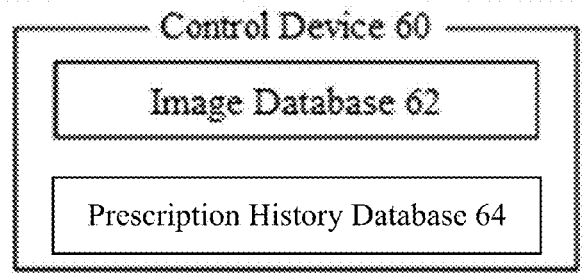
FIG. 2(b) is a block diagram showing a control device.

The medicine inspection device 10 is a device which inspects the quantity and type of single package portions of medicine targeted for inspection, the medicine thereof being supplied in a state of being divided and packaged in single dose portions in separate packaging paper. As shown in FIG. 2(*a*), the medicine inspection device 10 has an introduction unit 10*b* for introducing the medicine targeted for inspection to the side surface of a housing 10*a*, and has an operation panel 10*c* at the front surface. The medicine is packaged in translucent separate packaging paper, and is supplied to the medicine inspection device 10 in a state of being visible from the outside. Moreover, the medicine inspection device 10 is capable of supplying divided packaging bags in a state of a continuous divided packaging bag body for which a plurality of divided packaging bags in which single dose portions of medicine are packaged is continuously formed, and is capable of sequentially inspecting each divided packaging bag.

Figure 4:
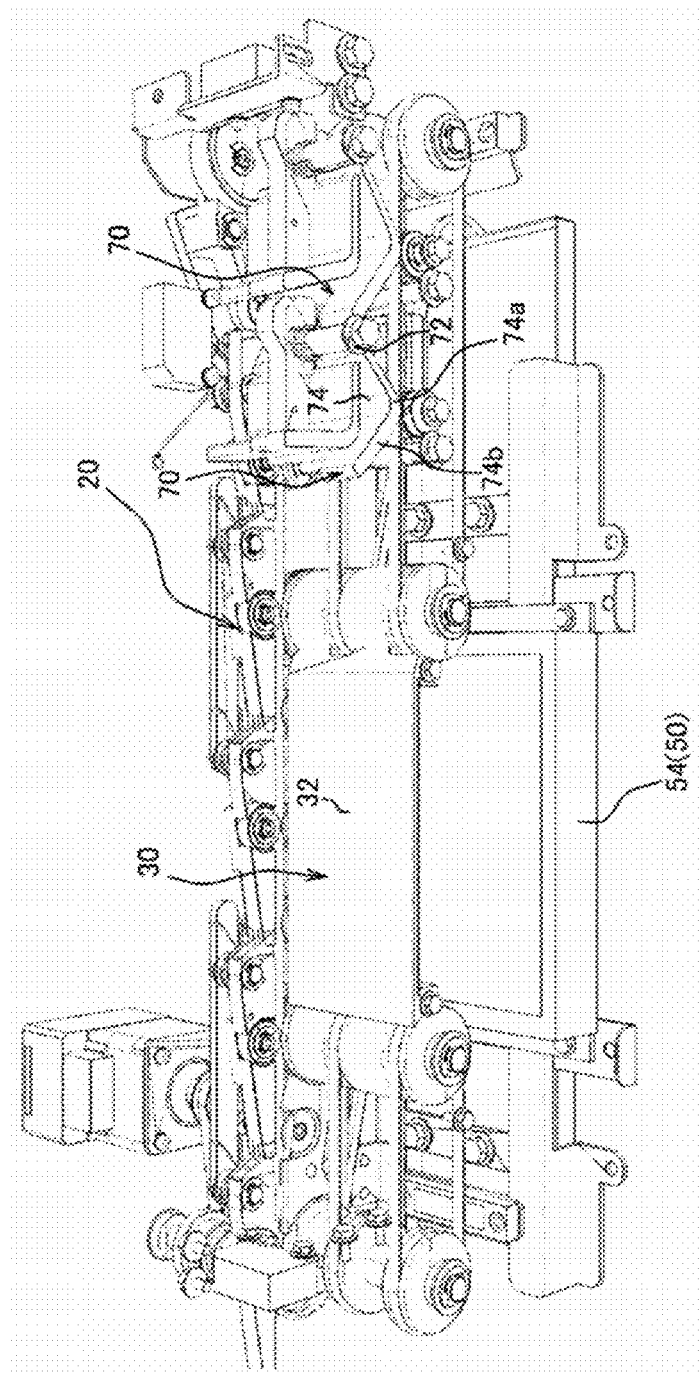
FIG. 4 is a perspective view showing the structure around the inspection unit of the medicine inspection device.

As shown in FIG. 2(*a*) to FIG. 4, the medicine inspection device 10 is provided with a conveying means 20, an inspection unit 30, a photographing device 40, an illumination device 50, a control device 60, and the like. The conveying means 20 is for taking in and conveying the continuous divided packaging bag body in which medicine is divided and packaged. The conveying means 20 can be formed of a conventionally known belt conveyor, roller conveyor, and the like. In the present embodiment, a belt conveyor is adopted as the conveying means 20. If a continuous divided packaging bag body formed by separate packaging paper is detected by a supply detector (not illustrated) provided at the upstream side in the conveyance direction with respect to the inspection unit 30, the conveying means 20 operates under the control of the control device 60, which will be described in detail below, and sequentially conveys the continuous divided packaging bag body to the downstream side. Moreover, if a discharge detector (not illustrated) provided at the downstream end confirms that the end of the continuous divided packaging bag body of the separate packaging paper is discharged further to the downstream side than the inspection unit 30, the operation of the conveying means 20 is stopped.

Figure 3:
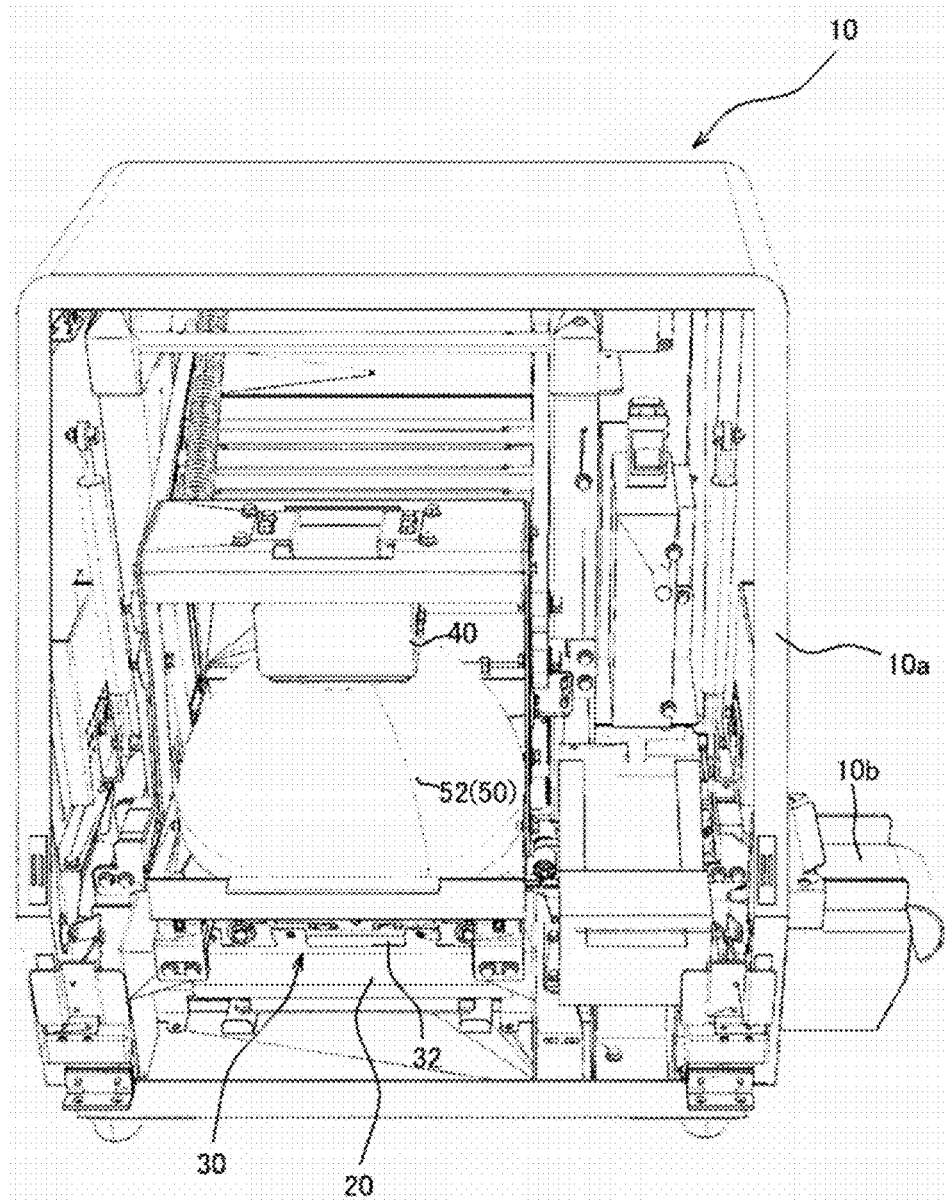
FIG. 3 is a perspective view showing the internal architecture of the medicine inspection device shown in FIG. 2(a).

The inspection unit 30 is a portion at which medicine to be inspected is arranged in a state of being contained in a divided packaging bag. As shown in FIG. 4, the inspection unit 30 has a photographing stage 32 at which divided packaging bags are arranged. The photographing stage 32 is formed by a translucent plate body, and is of a size that enables divided packaging bags of single package portions to be placed thereupon. The photographing device 40 is a device for photographing divided packaging bags arranged at the inspection unit 30 as well as medicine contained in those bags. As shown in FIG. 3, the photographing device 40 is arranged directly above the inspection unit 30.

The illumination device 50 is a device for illuminating divided packaging bags arranged at the inspection unit 30. The illumination device 50 has a front side illumination device 52 (see FIG. 3) and a back side illumination device 54 (see FIG. 4). The front side illumination device 52 is used to illuminate divided packaging bags arranged at the inspection unit 30 from the photographing device 40 side, namely, from above the inspection unit 30. The front side illumination device 52 may be configured of any type of illumination device, but with the present embodiment, an illumination device capable of producing diffused light is used. The back side illumination device 54 is used to illuminate divided packaging bags arranged at the inspection unit 30 from the back side, namely from a side opposite (downward) the photographing device 40 via the inspection unit 30. The back side illumination device 54 covers a region that illuminates roughly the entire photographing stage 32, and is capable of illuminating an entire divided packaging bag placed on the photographing stage 32 from the back side.

The control device 60 is realized on a computer by installing software on the computer. The control device 60 is capable of executing processing such as medicine inspection processing to inspect whether the medicine contained in each divided packaging bag is in accordance with a prescription, and supply control processing to supply the continuous divided packaging bag body for which divided packaging bags are continuously formed in a strip shape to the medicine inspection device 10. Medicine inspection processing and supply control of the continuous divided packaging bag body are described below.

<<Medicine Inspection Processing>>

The control device 60 is provided with an inspection database 62 which accumulates images of medicine as master images. The control device 60 executes processing (image matching processing) to match a master image registered in the inspection database 62 with an image of the medicine obtained by the photographing device 40, and can implement an inspection operation to inspect whether or not a medicine is packaged in a divided packaging bag in accordance with a prescription. More specifically, the control device 60 can implement an inspection (medicine type comparison inspection) to inspect the type of the medicine divided and packaged in the divided packaging bag, and can implement an inspection (quantity comparison inspection) to inspect the quantity of the medicine packaged in the divided packaging bag. By executing a medicine type comparison inspection, the control device 60 is capable of determining (medicine type match determination) whether or not the type of the divided and packaged medicine matches the prescription, and is capable of determining (similarity determination) whether or not a medicine (similar medicine) similar to the medicine packaged in the divided packaging bag is present in the inspection database 62 by executing image matching processing, and if a similar medicine is present, the control device 60 is capable of issuing an alarm. In other words, a medicine type match determination and similarity determination are implemented by executing the medicine type comparison inspection. Moreover, by implementing a quantity comparison inspection, the control device 60 can detect the quantity of medicine packaged in a divided packaging bag, and can determine (quantity determination) whether or not the medicine has been divided and packaged in a quantity that is in accordance with the prescription.

The medicine inspection device 10 has a plurality of the above-described similarity determination implementation modes. The operation mode of the medicine inspection device 10 may be set such that both the medicine type comparison inspection that includes a similarity determination, and the quantity comparison inspection are implemented, or such that only the quantity comparison inspection is implemented, and the operation mode may be optionally selected. The operation modes set at the medicine inspection device 10 are described in detail below.

Figure 8:
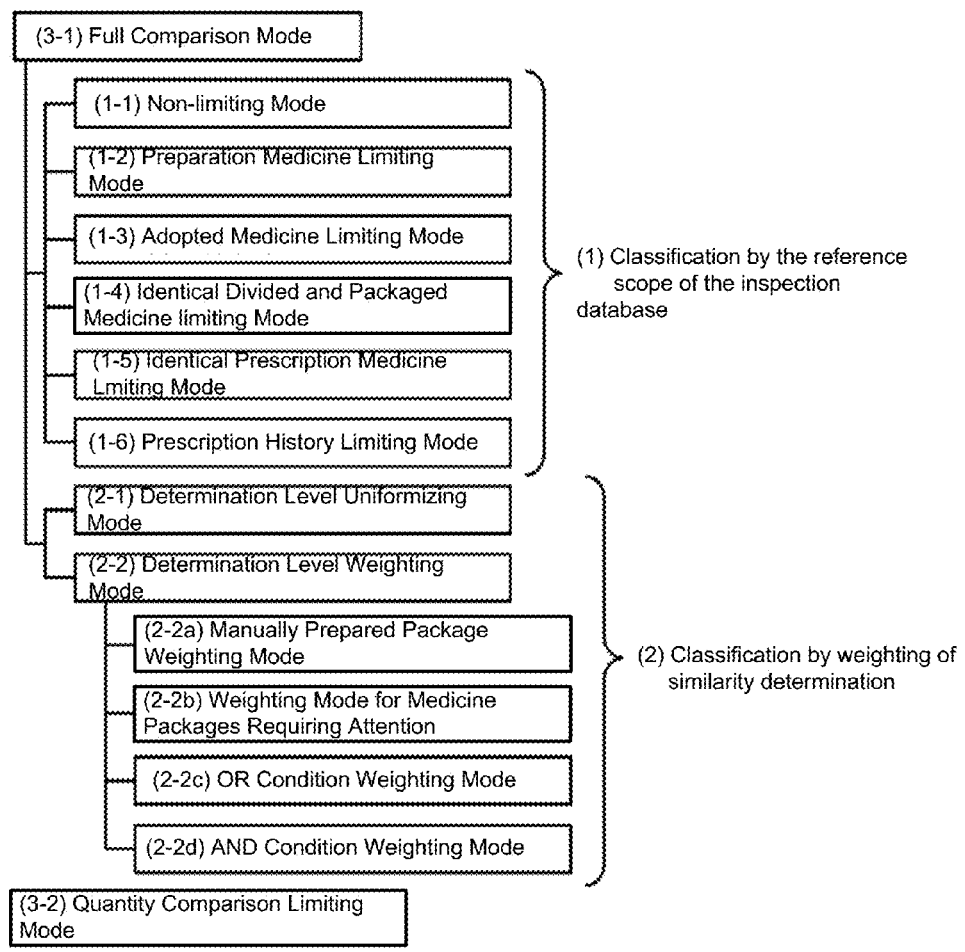
FIG. 8 is an explanatory diagram which schematically illustrates the relationship of the modes which implement medicine inspection processing.

As shown in FIG. 8, a plurality of operations modes can be set for the medicine inspection device 10 based on (1) the perspective of the reference scope of the inspection database, (2) the perspective of similarity determination weighting, and (3) the perspective of implementing or not implementing the medicine type comparison inspection. Operations at the medicine inspection device 10 can be executed in accordance with a user's requests by the user selecting the operation mode which is set based on these perspectives.

First, the operation mode classification based on (1) the perspective of the reference scope of the inspection database is explained. Six operation modes are set at the medicine inspection device 10 in accordance with the reference scope of the inspection database that is referenced when similarity determination is implemented. Those operation modes are (1-1) a non-limiting mode, (1-2) a preparation medicine limiting mode, (1-3) an adopted medicine limiting mode, (1-4) an identical divided and packaged medicine limiting mode, (1-5) an identical prescription medicine limiting mode, and (1-6) a prescription history limiting mode. Each mode is described below.

(1-1) Non-Limiting Mode

Similarity determination through the non-limiting mode is implemented with all medicines registered in the inspection database 62 as the reference scope. If similarity determination is implemented through the non-limiting mode, all medicines registered in the inspection database 62 can be used as the target of similarity determination without exception.

(1-2) Preparation Medicine Limiting Mode

If similarity determination is implemented through the preparation medicine limiting mode, similarity determination is implemented with the reference scope of the inspection database 62 limited to within a scope of medicines registered as medicines to be packaged for dividing and packaging at the medicine dividing and packaging device 100 (hereinafter, also referred to as "prepared medicines 300" (See FIG. 5(a)). Here, prepared medicines 300 include medicines to be packaged using a cassette or the like for dividing and packaging at the medicine dividing and packaging device 100, as well as overall medicines registered as medicines to be packaged. In other words, the phrase prepared medicines 300 is a concept that includes medicines which cannot be packaged at the medicine dividing and packaging device 100 but are prepared in a separate cassette or the like, medicines requiring cold storage and prepared using a cassette or the like in preparation for packaging by the medicine dividing and packaging device, and medicines which are not packaged but are used in dividing and packaging such as medicines prepared by the manual medicine supply unit 138 for dividing and packaging (hereinafter, also referred to as "manually dispersed medicines".

When the preparation medicine limiting mode is selected, the reference scope of the inspection database 62 is limited compared to when similarity determination is implemented with the non-limiting mode. Namely, the preparation medicine limiting mode is an operation mode that implements similarity determination excluding medicines, which are not prepared as medicines to be divided and packaged by the medicine dividing and packaging device 100 of which are assumed to have a low potential for erroneous dividing and packaging, as the target for similarity determination. Accordingly, an excessive determination of the presence of similar medicines through similarity determination can be suppressed, and the frequency at which reinspection by a pharmacist or the like is required can be minimized by implementing similarity determination through the preparation medicine limiting mode. In other words, regardless of whether a medicine may have an extremely low possibility of being erroneously divided and packaged, the problem of an alarm being generated or the like for the presence of a similar medicine is suppressed, and the cumbersomeness of the inspection operation can be resolved. Moreover, because the reference scope of the inspection database 62 is limited to prepared medicines 300 for the similarity determination, the speed of processing required for similarity determination can be improved, and the operation efficiency of the inspection operation can be further improved.

(1-3) Adopted Medicine Limiting Mode

The adopted medicine limiting mode is an operation mode that implements similarity determination with the reference scope of the inspection database 62 limited to within a scope of medicines that are registered as medicines prepared for dividing and packaging (hereinafter, also referred to as "adopted medicines") from amongst the medicines registered in the inspection database 62 (see FIG. 5(b)). Here, the phrase adopted medicines is a concept that includes not only medicines packaged and prepared for dividing and packaging at the medicine dividing and packaging device, but also overall medicines registered and assumed to be medicines that will be used in dividing and packaging. More specifically, adopted medicines include medicines that are actually packaged or prepared for packaging using the medicine dividing and packaging device, as well as overall medicines adopted for dividing and packaging within a pharmacy or other facility or within a pharmacy chain. Accordingly, if the medicine dividing and packaging device 100 is not provided with a manual medicine supply unit 138, prepared medicines 300 correspond to adopted medicines, and the adopted medicine limiting mode and the preparation medicine limiting mode are essentially the same operating mode.

When the adopted medicine limiting mode is selected as well, the reference scope of the inspection database 62 is limited compared to when similarity determination is implemented with the non-limiting mode. With the adopted medicine limiting mode, medicines which are not adopted for dividing and packaging by the medicine dividing and packaging device 100 and for which there is a very low possibility of erroneous dividing and packaging are excluded from the target for similarity determination, and as a result, the problems of alarms being generated for the presence of medicines other than adopted medicines 301 as similar medicines and of the need for a visual re-inspection by a pharmacist or the like can be resolved. Furthermore, by narrowing down the reference scope of the inspection database 62, the speed of processing required for similarity determination, and the operational efficiency of the inspection operation can be improved.

(1-4) Identical Divided and Packaged Medicine Limiting Mode

The identical divided and packaged medicine limiting mode is an operation mode for similarity determination that limits the reference scope of the inspection database 62 to within a scope of medicines 302 packaged in a divided packaging bag (see FIG. 5(c)). By selecting the identical divided and packaged medicine limiting mode, the reference scope of the inspection database 62 is significantly limited compared to when the non-limiting mode is selected. As a result, the matter of an alarm being generated for the presence of a similar medicine can be significantly suppressed, and the cumbersomeness of the inspection operation can be resolved. Moreover, by narrowing down the reference scope of the inspection database 62 in this manner, the speed of processing required for similarity determination can be improved.

(1-5) Identical Prescription Medicine Limiting Mode

The identical prescription medicine limiting mode is an operation mode for implementing similarity determination with the reference scope of the inspection database 62 limited to within a scope of medicines 303 divided and packaged in a divided packaging bag group prepared for prescriptions of the same patient (see FIG. 5(*d*)). When the identical prescription medicine limiting mode is selected as well, the reference scope of the inspection database 62 is significantly limited compared to when the non-limiting mode is selected, and the matter of an alarm indicating the presence of a similar medicine being generated more than is necessary can be avoided. Furthermore, the cumbersomeness of the inspection operation can be resolved, and the speed of processing required for similarity determination can be improved.

(1-6) Prescription History Limiting Mode

When the prescription history limiting mode is selected, a database in which the prescription history for the patient corresponding to the divided packaging bag targeted for inspection is registered (prescription history database 64) is referenced (see FIG. 5(*e*)), and medicines registered as the prescription history (hereinafter, also referred to as "existing prescription medicines 304") are specified. In the prescription history limiting mode, similarity determination is implemented with the reference scope of the inspection database 62 limited to existing prescription medicines 304.

Next, the classification of the operation mode based on (2) the perspective of similarity determination weighting is described. At the medicine inspection device 10, two types of operation modes, the (2-1) determination level uniformizing mode and the (2-2) determination level weighting mode, are set based on the perspective of similarity determination weighting. Each mode is described in detail below.

(2-1) Determination Level Uniformizing Mode

The determination level uniformizing mode is an operation mode that implements similarity determination with the reference scope of the inspection database 62 set to the same scope for all single divided packaging bag groups divided and packaged based on the same prescription. In other words, when the determination level uniformizing mode is selected, similarity determination is performed by an optional operation mode selected from the operation modes (1-1) to (1-6) described above for all divided packaging bags that form a divided packaging bag group.

(2-2) Determination Level Weighting Mode

The determination level weighting mode is an operation mode that dissimilates the reference scope of the inspection database 62 in a similarity determination between when an inspection is performed for divided packaging bags that form a portion of the divided packaging bag group and when an inspection is performed for other divided packaging bags. In the determination level weighting mode, any of four operation modes can be selected and implemented according to the selection method for the divided packaging bag that expands the reference scope of the inspection database 62 and increases the determination level of similarity determination to a level that is higher than the others. Those four operation modes include (2-2a) a manually prepared package weighting mode, (2-2b) a weighting mode for medicine packages requiring attention, (2-2c) an OR condition weighting mode, and (2-2d) an AND condition weighting mode. In other words, in the present embodiment, as a subordinate concept of the determination level weighting mode, the two operation modes of the manually prepared package weighting mode and the weighting mode for medicine packages requiring attention can be selected according to the divided packaging bag for which the determination level of similarity determination is increased. Each operation mode configuring the determination level weighting mode is described below.

(2-2a) Manually Prepared Package Weighting Mode

Figure 6A:
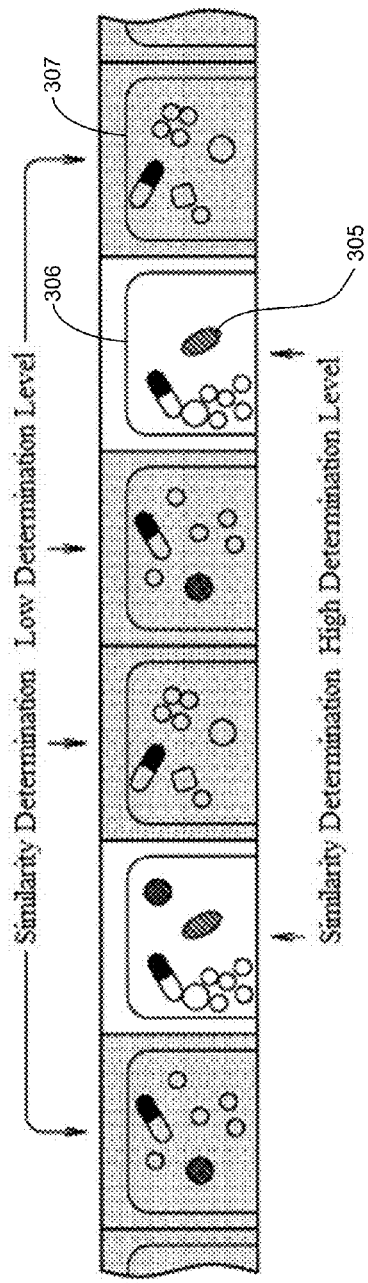
FIGS. 6(a) and (b) are an explanatory diagram which conceptually shows the application of similarity determination weighting of each divided packaging bag targeted for similarity determination, FIG. 6 (a) shows conditions during manually prepared package weighting mode, and FIG. 6 (b) shows conditions during weighting mode for medicine packages requiring attention.

The manually prepared package weighting mode is an operation mode that sets the determination level for packages containing medicines prepared manually by the manual medicine supply unit 138 (manually prepared medicines 305) to a higher level than the determination level of other divided packaging bags 307 when the determination level weighting mode is selected and a divided packaging bag in which manually prepared medicines 305 are packaged (hereinafter, also referred to as "package containing manually prepared medicines 306") is present. More specifically, similarity determination is executed with the reference scope of the inspection database 62, which is referenced when a similarity determination is implemented for divided and packaged manually prepared medicines 305 like the divided packaging bags not shaded in FIG. 6(*a*), expanded to a broader scope than the reference level when similarity determination for a divided packaging bag not containing manually prepared medicines 305 like the divided packaging bags shaded in FIG. 6(*a*) is implemented.

The difference in the range of the reference scope of the inspection database 62 (the sensitivity of the determination level) can be realized by dissimilating the operation mode through the above-described (1) perspective of the reference scope of the inspection database depending on whether or not the divided packaging bag targeted for inspection is a package containing manually prepared medicines 306. In this embodiment, the operation mode is selected such that similarity determination is performed through the above-described (1-2) preparation medicine limiting mode for packages containing manually prepared medicines, and similarity determination is performed through the (1-4) identical divided and packaged medicine limiting mode for other divided packaging bags 307, and weighting of the determination level is performed.

The manually prepared package weighting mode is an operation mode that is provided with consideration of the increased risk of the occurrence of erroneous dividing and packaging when medicines are prepared manually for divided packaging bags in which medicines prepared by the manual medicine supply unit 138 are packaged. By selecting this operation mode, the determination level for similarity determination regarding divided packaging bags in which medicines prepared by the manual medicine supply unit 138 are packaged is set to a higher level than the determination level for other divided packaging bags 307. Through this, similarity determination can be implemented with weighting applied to the divided packaging bags containing manually prepared medicines 305 that require attention in the inspection process.

(2-2b) Weighting Mode for Medicine Packages Requiring Attention

Figure 6B:
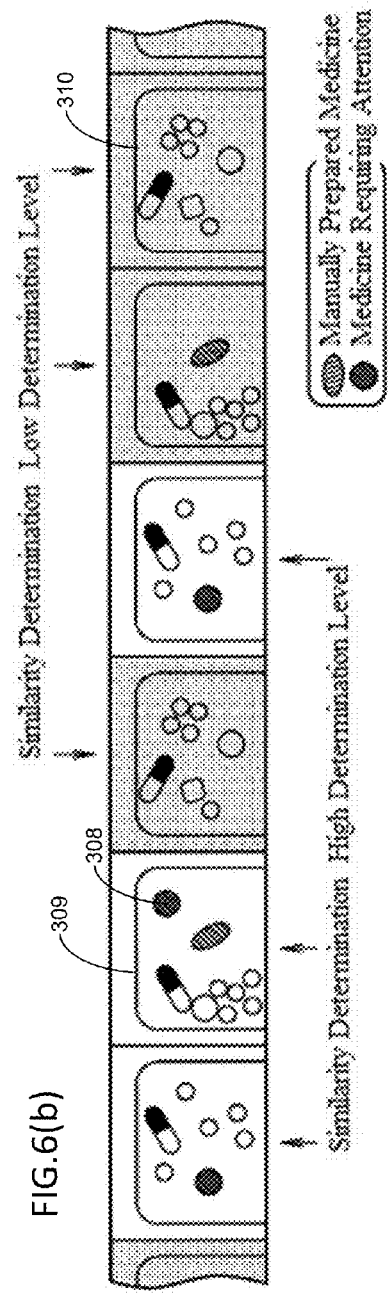

The weighting mode for medicine packages requiring attention is an operation mode that can be implemented by preselecting optional medicines from amongst medicines registered in the inspection database 62 as medicines 308 requiring caution (medicines requiring control). Medicines 308 requiring caution may be preselected when the inspection database 62 is constructed, or may be selected by the user. By selecting the weighting mode for medicine packages requiring attention, similarity determination can be implemented for divided packaging bags in which medicines selected as medicines requiring attention are packaged (hereinafter, also referred to as "packages 309 containing medicines requiring attention") with greater weighting applied than similarity determination for other divided packaging bags 310. More specifically, similarity determination is performed with the reference scope of the inspection database 62 when inspecting divided packaging bags not containing medicines requiring attention as shaded in FIG. 6(b) is set to a broader scope than the reference scope when inspecting divided packaging bags containing medicines requiring attention as shaded in the same figure.

Similar to the above-described case of the (2-2a) manually prepared package weighting mode, the difference in the range of the reference scope of the inspection database 62 (the sensitivity of the determination level) can be realized by dissimilating the operation mode set through the above-described (1) perspective of the reference scope of the inspection database depending on whether or not the divided packaging bag targeted for inspection is a package containing manually prepared medicines 306. In this embodiment, the operation mode is selected such that similarity determination is performed through the above-described (1-2) preparation medicine limiting mode for packages containing manually prepared medicines, and similarity determination is performed through the (1-4) identical divided and packaged medicine limiting mode for other divided packaging bags 307, and weighting of the determination level is performed. With the present embodiment, the operation mode is selected such that similarity determination is performed through the above-described (1-2) preparation medicine limiting mode for packages 309 containing medicines requiring attention, and similarity determination is performed through the (1-4) identical divided and packaged medicine limiting mode for other divided packaging bags 310, and weighting of the determination level is performed.

By selecting the weighting mode for medicine packages requiring attention, effective utilization can be achieved, for example, for cases in which medicines are present for which erroneous dividing and packaging could be a problem. In other words, similarity determination can be implemented with weighting applied to divided packaging bags containing medicines that require caution in the inspection process by preselecting medicines requiring attention as medicines 308 requiring caution and operating with the weighting mode for medicine packages requiring attention.

(2-2c) OR Condition Weighting Mode

The OR condition weighting mode is an operation mode for which the determination level for similarity determination for both packages containing manually prepared medicines and packages containing medicines requiring attention is set higher than the determination level for other divided packaging bags. In other words, the OR condition weighting mode is an operation mode that sets the determination level when inspecting packages containing manually prepared medicines or packages containing medicines requiring attention to a higher level than the determination level when inspecting other divided packaging bags, and could be called a mode that implements both the above-described (2-2a) manually prepared package weighting mode and (2-2b) weighting mode for medicine packages requiring attention all at once.

Figure 7A:
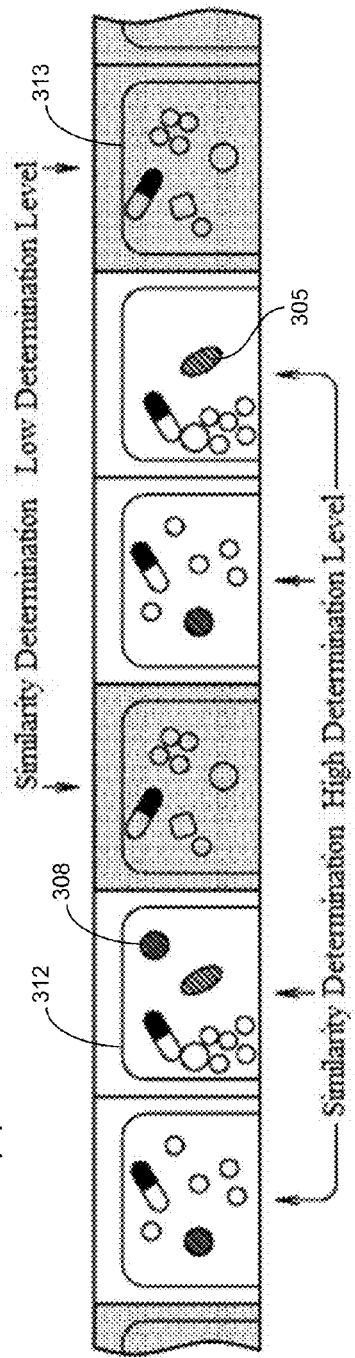
FIGS. 7(a) and (b) are an explanatory diagram which conceptually shows the application of similarity determination weighting of each divided packaging bag targeted for similarity determination, FIG. 7 (a) shows conditions during an OR condition weighting mode, and FIG. 7 (b) shows conditions during an AND condition weighting mode.

With the OR condition weighting mode, the determination level for similarity determination regarding one of either manually prepared medicines 305 that have been divided and packaged or medicines 308 requiring attention that have been divided and packaged as shown by the non-shaded packages 312 in FIG. 7(a) is set higher than the determination level for other divided packaging bags. More specifically, similarity determination is implemented with the reference scope of the inspection database 62 that is referenced during similarity determination regarding divided packaging bags that are not shaded in FIG. 7(a) set to a broader scope than the reference level when implementing similarity determination of the shaded divided packaging bags 313.

Similar to the above-described cases of the (2-2a) manually prepared package weighting mode and (2-2b) weighting mode for medicine packages requiring attention, the difference in the range of the reference scope of the inspection database 62 (the sensitivity of the determination level) can be realized by dissimilating the operation mode set through the above-described (1) perspective of the reference scope of the inspection database. In this embodiment, the operation mode is selected such that similarity determination is performed through the above-described (1-2) preparation medicine limiting mode for packages containing manually prepared medicines and packages containing medicines requiring attention, and similarity determination is performed through the (1-4) identical divided and packaged medicine limiting mode for other divided packaging bags, and weighting of the determination level is performed.

(2-2d) AND Condition Weighting Mode

The AND condition weighting mode is an operation mode which sets the determination level for similarity determination of divided packaging bags 314 that are packages containing manually prepared medicines 305 that are also packages containing medicines 308 requiring attention, to a higher level than the determination level for other divided packaging bag. In other words, the AND condition weighting mode is an operation mode that sets the determination level when inspecting divided packaging bags 314 containing both manually prepared medicines 305 and medicines 308 requiring attention to a higher level than the determination level when inspecting other divided packaging bags 315.

Figure 7B:
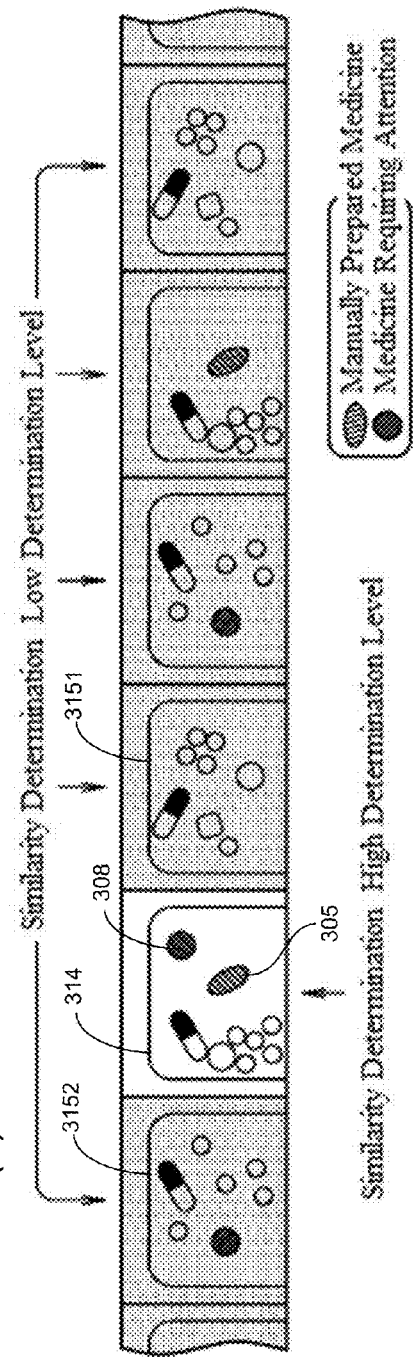

With the AND condition weighting mode, the determination level for the divided packaging bags 314 that are shaded in FIG. 7(b) is set lower than the determination level for the non-shaded divided packaging bags 314 that contain both manually prepared medicines 305 and medicines 308 requiring attention. More specifically, as shown in FIG. 7(b), the determination level for divided packaging bags 3151 not containing both manually prepared medicines 305 and medicines 308 requiring attention and the determination level for divided packaging bags 3152 containing only either manually prepared medicines 305 or medicines 308 requiring attention are set to a level that is lower than the determination level for divided packaging bags 314 containing both.

The difference in the range of the reference scope of the inspection database 62 (the sensitivity of the determination level) is similar to the above-described cases of the (2-2a) manually prepared package weighting mode, (2-2b) weighting mode for medicine packages requiring attention, and (2-2c) OR condition weighting mode. In this embodiment, the operation mode is selected such that similarity determination is performed through the (1-2) preparation medicine limiting mode for divided packaging bags 314 that are packages containing manually prepared medicines that are also packages containing medicines 308 requiring attention, and similarity determination is performed through the (1-4) identical divided and packaged medicine limiting mode for other divided packaging bags 315, and weighting of the determination level is performed.

Next, classification of the operation mode through (3) the perspective of implementing or not implementing the medicine type comparison inspection is explained. As described above, the medicine inspection device 10 is capable of implementing a medicine type comparison inspection which includes a similarity determination and a medicine type match determination, and a quantity comparison inspection, which determines whether the quantity of the medicine divided and packaged in the divided packaging bag is in accordance with the prescription. At the medicine inspection device 10, a (3-1) full comparison mode and a (3-2) quantity comparison limited mode can be selected and implemented according to whether the medicine type comparison inspection is implemented or not implemented. The (3-1) full comparison mode is an operation mode which implements both the medicine type comparison inspection and the quantity comparison inspection, and the (3-2) quantity comparison limited mode is an operation mode which implements only the quantity comparison inspection without implementing the medicine type comparison inspection. By providing a quantity comparison limited mode in this manner, a quantity comparison inspection can be implemented while omitting the medicine type comparison inspection that includes a similarity determination, and the excessive determination regarding the presence of similar medicines can be avoided in the inspection operation.

When executing an inspection operation, the medicine inspection device 10 can select and implement an arbitrary operation mode from a plurality of operation modes configured from the above described (1) perspective of the reference scope of the inspection database 62, (2) perspective of similarity determination weighting, and (3) perspective of implementing or not implementing the medicine type comparison inspection. More specifically, if the (3-1) full comparison mode is selected from the (3) perspective of implementing or not implementing the medicine type comparison inspection, the (1-1) non-limiting mode can be selected as the operation mode for similarity determination from the (1) perspective of the reference scope of the inspection database 62, the (2-2) determination level weighting mode can be selected from the (2) perspective of the implementation range of similarity determination weighting, and the operation mode can thereby be arbitrarily set. Note that if the (3-2) quantity comparison limited mode is selected, similarity determination is not implemented, and therefore selection of the operation mode through (1) the perspective of the reference scope of the inspection database 62 and (2) the perspective of similarity determination weighting is not generated. Moreover, with the present embodiment, examples for which a plurality of operation modes were prepared through (1) the perspective of the reference scope of the inspection database 62 and (2) the perspective of similarity determination weighting as the modes for implementing similarity determination were presented, but the present invention is not limited thereto, and a single operation mode may be prepared for one or both of the perspectives of (1) and (2) such that a selection is not generated.

<<Supply Control of the Continuous Divided Packaging Bag Body>>

The medicine inspection device 10 can cause a sequentially divided packaging bag to arrive at the inspection unit 30 by supplying the divided packaging bags in the form of a continuous divided packaging bag body that is a continuous strip shape, and can then inspect the sequentially divided packaging bag thereof. Here, if the divided packaging bags that form the continuous divided packaging bag body are of the same length in the longitudinal direction of the continuous divided packaging bag body, each time the inspection of each divided packaging bag is completed at the inspection unit 30, a prescribed length only of the continuous divided packaging bag body may be fed. However, when the length of the continuous divided packaging bag body that is fed each time an inspection is completed is uniform but the length of each of the divided packaging bags that form the continuous divided packaging bag body is not uniform, the divided packaging bag targeted for inspection may be positionally deviated with respect to the inspection unit 30, and the possibility of not being able to conduct an accurate inspection increases.

Therefore, in order to eliminate the above-described problem, it is preferable that the length of each divided packaging bag that forms the continuous divided packaging bag body be understood in advance by the control device 60, and that control be executed to adjust the feed length of the continuous divided packaging bag body in accordance with the length of the divided packaging bag. Data regarding the length of each continuous divided packaging bag body can be understood by the control device 60 using an appropriate method such as specifying said data for each divided packaging bag by a pharmacist or the like, stipulating said data by providing and reading an identification means such as a barcode or tag at an appropriate location such as at a front end position of the continuous divided packaging bag body, or stipulating the length of the continuous divided packaging bag body through interlocking with the medicine dividing and packaging device 100.

<<Dichromic Determination Processing>>

Here, in order to improve the inspection precision at the medicine inspection device 10 of medicines which have a long shape in a prescribed direction and for which the color is different with a center part in the longitudinal direction as a boundary (hereinafter, also referred to as "long medicines 316") as shown in FIG. 10(a), dichromic determination processing can be executed. In the present embodiment, specific examples of medicines targeted for the implementation of dichromic determination processing include medicines called capsule agents or caplet agents, which are tablets which model the shape and size of capsules. An overview of dichromic determination processing is described in a simple manner below, after which the implementation method is described with focus on the key portions of the processing.

When the medicine type is inspected (medicine type comparison inspection) at the medicine inspection device 10, in addition to a comparison of the size and shape of the medicine, a comparison of the color of the medicine is also implemented. When a comparison of the color of the medicine is implemented, a region corresponding to the medicine (medicine region 317) in the image (photograph image) obtained by photographing the medicine contained in the divided packaging bag is extracted, and an average value for the color data of the entire extracted medicine region 317 is calculated. Master information for the color data of each medicine is registered in the inspection database 62. The control device 60 compares the average value of the color data calculated from the photograph image with the master information registered in the inspection database 62, and can narrow down the type of the medicine photographed in the photograph image from a color perspective.

Long medicines 316 such as capsule agents that are targeted for dichromic determination processing here often have colors that differ with a center part in the longitudinal direction as the boundary between the colors. Therefore, it is assumed that for long medicines 316, rather than deriving an average value for the color data for the entire medicine region 317 and implementing a comparison, the inspection precision can be better improved by deriving separate average values for the color data of one side and the other side with the center part in the longitudinal direction as the boundary where the color changes, and then implementing a comparison regarding each of the average values thereof. Therefore, with the medicine inspection device 10, if the medicine to be inspected is a long medicine, dichromatic determination processing is implemented in accordance with the flowchart shown in FIG. 9.

Dichromic determination processing is implemented by deriving the region in which the medicine is present, and then deriving a region on one side and a region on the other side as respectively divided regions A and B with the roughly center part in the longitudinal direction of the medicine as the boundary between the two regions, after which, color data computational processing, comparison processing, and the like are performed for each divided region A and B. More specifically, the divided regions A and B are derived through four steps, which will be described in detail below, including a medicine region 317 derivation step (Step 1-1), a region position and orientation information derivation step (Step 1-2), a region shifting step (Step 1-3), and a divided region derivation step (Step 1-4).

In addition, image processing is also implemented through the same technique as that used to derive the divided regions A and B such that the image of long medicines 316 contained in a photograph image faces the horizontal direction in the center of the screen 318. More specifically, image processing is implemented through three steps that will be described in detail below including a medicine image derivation step (Step 1-5), an image position and orientation information derivation step (Step 1-6), and an image shifting step (Step 1-7). Next, a color information computational processing step (Step 1-8) is executed to compute color data in the regions corresponding to each of the divided regions A and B obtained in Step 1-4 for the image obtained after shifting in Step 1-7, and to derive average values thereof. Next, a comparison processing step (Step 1-9) is implemented based on the data obtained in Step 1-8.

As a more detailed description of each of the abovementioned steps, first, in the medicine region derivation step of Step 1-1, as shown in FIG. 10(a), the contour of a long medicine is extracted from an image (photograph image) obtained by photographing the divided packaging bag for the inspection, and the region within that contour is derived as the medicine region (the black colored region in FIG. 10(a)). Next, in the region position and orientation information derivation step of Step 1-2, as shown in FIG. 10(b), a rectangle 319 that circumscribes the medicine region is derived, and the center of gravity coordinates G(x,y) and angle θ of the long side thereof are derived.

In the region shifting step of Step 1-3, based on the center of gravity coordinates G(x,y) and angle θ of the long side derived above, the medicine region 317 derived in Step 1-1 is shifted to the center of the screen 318, and angular adjustments are made such that the medicine region 317 thereof is extended to the horizontal direction. Next, image processing is implemented in the divided region derivation step of Step 1-4 to divide the medicine region 317 shifted in Step 1-3 into two divided regions A and B. More specifically, after the medicine region 317 is shifted such that it is horizontal in the center of the screen 318 in Step 1-3, only the right side region of the medicine region 317 is extracted by implementing masking or the like to the left half of the screen 318 (see FIG. 10(e)). In this manner, the divided region A (right side divided region) is derived. Likewise, the right half of the screen 318 is masked or the like to derive the left side region of the medicine region 317 as the divided region B (left side medicine region 317) (see FIG. 10(d)).

When processing to derive the divided regions A and B is implemented through Step 1-1 to Step 1-4 as described above, image processing is implemented in each of Step 1-5 to Step 1-7 through a similar technique. More specifically, in the medicine image derivation step of Step 1-5, an image of the long medicines 316 photographed in the photograph image is identified in the same manner as the medicine region derivation step of Step 1-1. Next, the image position and orientation information derivation step of Step 1-6 executes processing similar to the region position and orientation information derivation step of Step 1-2 on the image of the long medicines 316. Namely, in Step 1-6, the center of gravity position and angle of the image of the long medicines 316 identified in Step 1-5 are derived.

The image shifting step of Step 1-7 performs processing similar to the region shifting step of Step 1-3 on the image of the long medicines 316. In Step 1-7, based on the center of gravity position and the tilt of the image of the long medicines 316 derived in Step 1-6, the image of the long medicines 316 is shifted to the center of the screen 318 and the angle is adjusted such that the longitudinal direction faces the horizontal direction.

Here, as described above, the long medicines 316 has respective colors on one side and the other side with the roughly center part in the longitudinal direction as a boundary. Therefore, in the color information computational processing step of Step 1-8, processing is executed to implement computation on color data within a region corresponding to the divided region A and on color data within a region corresponding to the divided region B in the image of the long medicines 316, and to derive average values for the respective divided regions A and B. More specifically, the average RGB values are derived for portions of the image of the long medicines 316 that correspond to the divided regions A and B. Next, an HSV conversion is implemented with respect to the RGB average values, and these converted values are used as average values of the HSV conversion. In this manner, the control device 60 obtains color information (RA, RB) for the divided regions A and B of the long medicines 316 that are the inspection target.

In Step 1-9, a comparison processing step is implemented based on data obtained in the above-described Step 1-8. In other words, as shown in FIG. 10(f), if one side in the longitudinal direction is designated as region α and the other side is designated as region with the roughly center part of the long medicines 316 as the boundary between the two sides, color information for regions α and β of the long medicines 316 are registered as master data in the inspection database 62 in the form of average HSV values. The control device 60 confirms whether the above-described color information (RA, RB) for each divided region A and B of the long medicines 316 that are the inspection target matches the combination of the master data (Mα, Mβ). In other words, if either (1) RA=Mα and RB=Mβ or (2) RA=Mβ and RB=Mα, then the color information (RA, RB) and the combination of the master data (Mα, Mβ) match. In this case, a determination is made that the long medicines 316 that are the inspection target is the medicine compared in the inspection database 62. On the other hand, if either of the conditions described in (1) or (2) does not apply, then a determination is made that the long medicines 316 that are the inspection target is different from the medicine compared in the inspection database 62. By repeating the data comparison in this manner for the long medicines 316 for which master data has been registered, the type of the medicine that is the inspection target can be identified.

By implementing dichromic determination processing as described above for a capsule agent or another long medicines 316, the medicine type match determination precision can be further improved through color for the long medicines 316. As a result, the inspection reliability regarding the medicine type can be improved. Moreover, an improvement in the precision of similarity determination is also anticipated when dichromic determination processing is utilized. Through this, medicines that could be determined to be similar medicines when it is assumed that a similarity determination has been performed by averaging the color of the overall long medicines 316, can be excluded from candidates for similar medicines by executing dichromic determination processing. Accordingly, the precision of similarity determination can also be improved by adopting dichromic determination processing.

Note that while not particularly mentioned in the above-described embodiment, the master data (Mα, Mβ) for the regions α and β of the long medicines 316 registered in the inspection database 62 can also be obtained using the method that was used to obtain the color information (RA, RB) of the divided regions A and B for medicine that is the inspection target. In other words, master data (Mα, Mβ) can be obtained and registered by processing an image for the long medicines 316 used for the above-described master registration with the procedures of Step 1-1 through Step 1-9.

<<Method for Determining that the Divided and Packaged Amount is Excessive Based on the Surface Area of the Medicine>>

Here, a case in which a total surface area Sm of medicine contained in a divided packaging bag is larger than a surface area Sp of one bag portion of the divided packaging bag that is the inspection target at the above-described medicine inspection device 10, or in other words, a case in which the ratio of surface areas Sm/Sp is close to one is assumed. If medicine is excessively divided and packaged in a single divided packaging bag in this manner, a phenomenon in which medicine is not dispersed even if vibration or such is applied to the divided packaging bag, and as a result, at the time of the inspection, the medicine is oriented in an upright state in the divided packaging bag, and a phenomenon for which the boundary between adjoining medicines cannot be accurately understood through image processing or the like are assumed. If these types of phenomena occur, even if a master database in which image information such as the surface shape, size, and color of a medicine has been registered for each medicine is compared with an image obtained by photographing a divided packaging bag that is the inspection target using the photographing device 40 in an attempt to inspect medicine in a divided packaging bag to determine whether it has been divided and packaged in accordance with a prescription, there is a possibility that sufficient precision will not be obtained. Therefore, in this type of case, the configuration is preferably such that the suggestion of a possibility of not being able to obtain sufficient inspection precision due to the medicine being excessively divided and packaged can be made to the user.

Therefore, the type and quantity of medicine that must be packaged based on prescription data is derived for the divided packaging bag that is the inspection target. In addition, if medicine is divided and packaged according to prescription data based on the master database, the total surface area of the medicinal product contained in a single divided packaging bag is derived as the theoretical surface area St. Moreover, a surface area for a portion of the divided packaging bag where medicine is contained (bag surface area Sp) is derived from data pertaining to the length (bag length) and width of the divided packaging bag. Furthermore, if the ratio of the theoretical surface area St with respect to the bag surface area Sp (Sp/St) exceeds a prescribed ratio α, a suggestion may be given to the user at a prescribed timing, such as when starting an inspection, that a possibility exists for not being able to obtain a sufficient inspection precision because the medicine is excessively divided and packaged in the divided packaging bag that is the inspection target. Note that as the suggestion method thereof, any method may be used as long as it is a method that can make a user aware of such possibility through, for example, a notification or the like implemented using an image, audio, or the like.

<<Method for Determining that the Divided and Packaged Amount is Excessive Based on the Volume of the Medicine>>

As measures to resolve similar issues, in addition to the above-described measure that is based on the bag surface area Sp and the theoretical surface area St, other measures can also be adopted such as, for example, a measure based on the volumes of the divided packaging bag and the medicine contained therein. More specifically, if it is determined based on the volume standard that medicine is excessively contained in the divided packaging bag to an extent that there is a possibility that sufficient inspection precision will not be obtained, the maximum quantity that can be divided and packaged in a divided packaging bag that is the inspection target (theoretical maximum quantity Nt) is understood for each medicine, and is registered in the master database and the like. The theoretical maximum quantity Nt is derived for each medicine through a theoretical method such as the quantity obtained by dividing the volume Vp of a single divided packaging bag portion by the volume Vm of a single portion of medicine (Nt=Vp/Vm), or by an experimental method or the like.

The volume per each single medicine unit can be derived by a method of measuring each medicine, and by a theoretical method. More specifically, a method that derives the shape of medicine from image data that shows a plan view state of each medicine registered in the master database, and then derives the volume of the medicine based on the planar shape of the medicine thereof can be adopted.

A method for deriving the volume of medicine based on the planar shape is as follows. Namely, if the medicine is a soft capsule having an exterior shape of a rugby ball, the planar shape of the medicine becomes elliptical. If the length of the long axis forming this elliptical shape is 'a' and the length of the short axis thereof is 'b,', the volume of the soft capsule can be derived by plugging in 'a' and 'b' into the mathematical equation $4\pi ab^2/3$.

If the medicine to be inspected is a capsule tablet, both ends have a hemispherical region, and the center part has a region that is cylindrical. Therefore, when the capsule tablet is observed from a plan view, both ends exhibit a semicircular shape, and the center part is a rectangular, planar shape. When the radius of the semicircular portion is r, and the length of the cylindrical portion is h, the volume of the capsule tablet can be derived by plugging r into the mathematical equation of $4\pi r^3/3+\pi r^2 h$, or in other words, $\pi r^2\{(4r/3)+h\}$. Moreover, if the medicine is a disc shape, the shape when viewed in a planar manner is roughly circular, and when the radius of the circle that forms the planar shape is r and the thickness of the medicine is d, the volume of the disc shaped medicine becomes $\pi r^2 d$. Accordingly, the volume of the disc shape medicine can be derived by plugging r and d into this mathematical equation.

If the containment ratio of the medicine with respect to the divided packaging bag is determined based on a volume standard, data like that described above is prepared in advance, and a volume Vn occupied by each medicine with respect to the volume Vp of the divided packaging bag that is the inspection target is derived for each medicine. In other words, a configuration can be adopted such that if n types of medicines are divided and packaged in a single divided packaging bag, the volumes V1, V2, . . . , Vn (n=a positive integer) occupied by each medicine are derived. Furthermore, if the ratio occupied by the total occupied volume ΣVn, which is the sum of the occupied volumes Vn, with respect to the volume Vp of the divided packaging bag is at or above a prescribed ratio, the medicine in the divided packaging bag that is the inspection target is excessively divided and packaged, and a determination is made that there is a possibility that sufficient inspection precision will not be obtained.

Note that even when this configuration and method are adopted, any method such as providing notification through images or audio may be adopted as the suggestion method as long as the method can make a user aware of the possible insufficient inspection precision. Furthermore, with the present method, a configuration was illustrated that performs a comparison with the volume Vp after the total occupied volume ΣVn is derived, but the present invention is not limited thereto. In other words, for example, a configuration may be adopted for which the ratio occupied by the occupied volume V1, V2, . . . , Vn (n=a positive integer) with respect to the volume Vp of the divided packaging bag is derived as an occupied rate P1, P2, . . . , Pn (n=a positive integer) for each medicine, and if the total occupied rate ΣPn, which is the sum thereof, exceeds a prescribed ratio, a determination is made that the medicine is excessively divided and packaged and thus there is a possibility that sufficient inspection precision will not be obtained. Furthermore, the method for theoretically deriving the volume of a medicine is not limited to the above-described method, and for example, the volume thereof may be derived by integrating the planar shape surface area of the medicine derived from the image data.

<<Method for Determining the Positioning Precision of a Divided Packaging Bag with Respect to the Inspection Unit 30 and a Position Correction Method>>

Here, the above-described medicine inspection device 10 conducts an inspection to determine whether a medicine has been divided and packaged in accordance with a prescription based on an image obtained by photographing the divided packaging bag targeted for inspection using the photographing device 40. Therefore, when the divided packaging bag is conveyed to the inspection unit 30, if the positioning precision of the divided packaging bag with respect to the inspection unit 30 is low, the inspection precision could also be low as well. Thus, if the configuration is such that divided packaging bags are supplied to the medicine inspection device 10 in the state of a continuous divided packaging bag body formed by a series of multiple divided packaging bags divided by perforations or another boundary, the occurrence of such problems can be suppressed in the following manner.

Figure 11A:
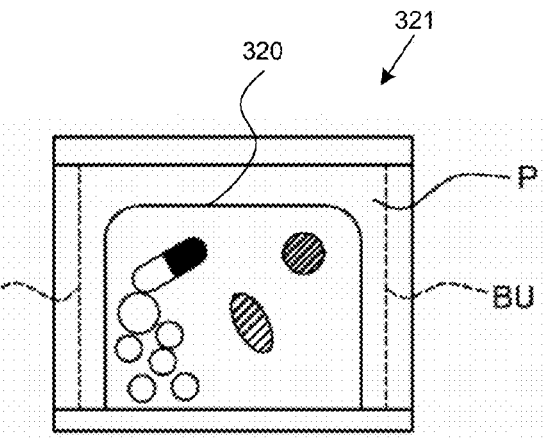
FIG. 11(a) to FIG. 11(c) are a diagram showing examples of photographed images for a case when inspection of a divided packaging bag supplied as a continuous divided packaging bag body is performed.
Figure 11B:
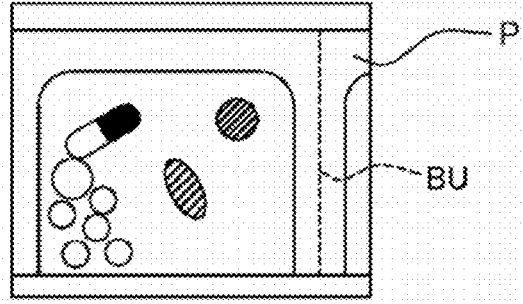
Figure 11C:
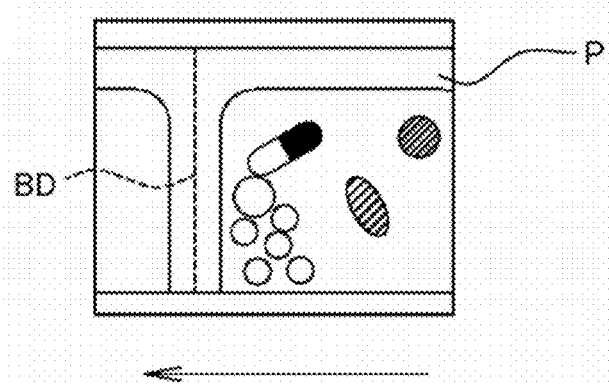

Namely, if an inspection is performed of a divided packaging bag supplied as a continuous divided packaging bag body, an image like that shown in FIG. 11(a) to FIG. 11(c) are photographed by the photographing device 40. Here, if the divided packaging bags 320 supplied to the inspection unit 30 are in a state of being positioned with good precision as shown in FIG. 11(a), both the perforations on the upstream side (boundary/reference symbol BU in FIG. 11) and the perforations on the downstream side (boundary/reference symbol BD in FIG. 11) in the conveyance direction (the direction shown by the arrow in FIG. 11) of the continuous divided packaging bag body (reference symbol P in FIG. 11) with respect to the divided packaging bags 320, which are the inspection target, are included in the photograph image 321 obtained by the photographing device 40, and an image for which the roughly center position of the inspection unit is positioned roughly in the center of the photograph image 321 is obtained.

Even if the configuration is as described above, if only one perforation line (boundary) is photographed in the image taken by the photographing device 40, it is conceivable that the divided packaging bags 320 is positionally deviated to the upstream side or the downstream side in the conveyance direction with respect to the inspection unit 30. Furthermore, as shown in FIG. 11(b), if only one perforation line (boundary) is photographed and it is shown in the photograph to be further downstream in the conveyance direction of the continuous divided packaging bag body than the center position of the inspection unit 30, it can be determined that the conveyance of the divided packaging bags 320 is shifted to the upstream side in the conveyance direction (the conveyance amount is insufficient). On the other hand, as shown in FIG. 11(c), if only one perforation line (boundary) is photographed and it is shown in the photograph to be further upstream in the conveyance direction of the continuous divided packaging bag body than the center position of the inspection unit 30, then it can be determined that the conveyance of the divided packaging bags 320 is shifted downstream in the conveyance direction (excessive conveyance amount).

Moreover, if only one perforation line (boundary) is photographed in the photograph image 321 obtained by the photographing device 40, a correction value for the conveyance amount of the divided packaging bags 320 can be derived from the values for the center position in the conveyance direction, the position of the perforation line (boundary), and the bag length of the divided packaging bags 320 in the photograph image 321. The position of the divided packaging bags 320 can then be shifted based on the correction value derived in this manner, and as a result, the divided packaging bags 320 can be positioned at the optimum position for inspection.

<<Method for Providing Notification of the Need for Master Image Registration Pertaining to Newly Adopted Medicine Products>>

Here, when a medicine is inspected at the medicine inspection device 10 to determine if it has been divided and packaged according to a prescription, if the configuration of the device is such that a master database in which image information such as the surface shape, size, and color of a medicine has been registered for each medicine is referenced, then, when newly adopted medicine products that have not been registered in the master database are divided and packaged, they cannot be correctly inspected. Therefore, if newly adopted medicine products are to be used, an image and information for that medicine must be registered in advance in the master database.

Moreover, as with the above-described system S for individually packaging medicines, if the configuration is such that a divided packaging bag (continuous divided packaging bag body) that has been divided and packaged at the medicine dividing and packaging device 100 is supplied to the medicine inspection device 10 for inspection, and if the configuration is such that an alarm is finally generated at the point in time when the divided packaging bag arrives at the medicine inspection device 10 to indicate that a newly adopted medicine product is contained, operation time will be lost. In other words, with this type of configuration, the operator becomes aware of the presence of a newly adopted medicine product when it arrives at the medicine inspection device 10, and therefore beginning at that point in time, the operator starts operations to register information about the newly adopted medicine product in the master database. As a result, the inspection process is stopped while the work to register the information is performed. Furthermore, even if dividing and packaging is continued at the medicine dividing and packaging device 100 while the information is being registered, those bags must be inspected, and the number of divided packaging bags waiting for inspection gradually increases. On the other hand, when dividing and packaging operations at the medicine dividing and packaging device 100 are stopped during the work to register the information, stagnation in the dividing and packaging operations occurs. Therefore, if a newly adopted medicine product for which the medicine information has not been registered in the master database is present, the user is preferably notified as quickly as possible of that presence. More specifically, notification of the presence of a newly adopted medicine product is preferably provided at the point in time when dividing and packaging are implemented at the medicine dividing and packaging device 100, or at a point in time that is even earlier, and at the very least, notification is preferably provided by the time that the divided packaging bag arrives at the medicine inspection device 10 after dividing and packaging have been performed at the medicine dividing and packaging device 100. Moreover, the method for providing the above-described notification can be one of either notification through audio or notification through an image, or the like, or notification may be provided through multiple measures by combining a plurality of these measures.

Furthermore, notification may also be provided at the medicine dividing and packaging device 100 in the system S for individually packaging medicine, but in some cases, it is preferable to provide notification at the medicine inspection device 10 side. More specifically, if the configuration is such that of the medicine information (exterior shape, size, color, image data, and the like) registered in the master database, at least a portion is derived and registered based on an image photographed by the photographing device 40 at the medicine inspection device 10, then providing notification at the medicine inspection device 10 side can better improve operational efficiency than providing notification at the medicine dividing and packaging device 100 side. In particular, if the distance between the medicine inspection device 10 and the medicine dividing and packaging device 100 is greatly separated in the system S for individually packaging medicine, then providing the notification at the medicine inspection device 10 side can significantly improve the operational efficiency.

Various items can be selected as targets for notification of the need to newly register information in the master database as described above. Namely, the above-described method can be adopted for all cases when notification regarding the need to register information in the master database becomes necessary including for cases such as when a medicine is a new product with absolutely no information registered in the master database, or when other data is already registered in the master database, but an image showing the exterior appearance is not registered, or the like.

<<Method for Registering Master Images Pertaining to Translucent Medicines>>

With inspections by the above-described medicine inspection device 10, image data showing the exterior shape of a medicine registered in the master database is used to perform a comparison. Therefore, in order to register master data of a medicine in the master database, the contour of the medicine must be understood with relative accuracy, and image processing such as cropping or the like becomes necessary. The following type of technique exists as a method for deriving the contour of a medicine.

Namely, when the contour of a medicine is derived, first, of the illumination device 50 that is used to illuminate a divided packaging bag arranged at the inspection unit 30, the back side illumination device 54 is used to illuminate the inspection unit 30, and in this state, an image (hereinafter, also referred to as a "backlight image 322") photographed of the medicine arranged on the inspection unit 30 by the photographing device 40 is obtained (see FIG. 12(a)). In addition, an image photographed of the divided packaging bag arranged at the inspection unit 30 with illumination by the front side illumination device 52 from the photographing device 40 is obtained (also referred to as the "front side image 323") (see FIG. 12(b)). While the illumination states of the backlight image 322 and the front side image 323 are different, the images thereof are photographed by the same photographing device 40. Therefore, the positional relationship of the regions contained in the backlight image 322 and the front side image 323 is a respectively corresponding relationship.

Here, as described above, the inspection unit 30 is configured with a translucent plate body. Therefore, the region in the backlight image 322 where the medicine is not arranged (the background region) is projected brightly in the photographed image with the light in a transmitted state. In contrast, if the medicine is not translucent, the region in the back light image where the medicine is arranged is projected in the photographed image as a dark, roughly black region. Therefore, if the medicine is not translucent, the contour of the medicine can be derived based on the difference in contrast in the backlight image 322.

More specifically, in the present embodiment, an illumination device that emits a red light is adopted as the back side illumination device 54. Therefore, when an image of the R component obtained by decomposing the backlight image into RGB is acquired, as shown in FIG. 12(c), a difference in shading between the background portion and the medicine portion becomes clear. When noise is removed from the image of FIG. 12(c), the image shown in FIG. 12(d) is obtained. Next, a region having a brightness that is lower than a prescribed brightness in the image of FIG. 12(d) is extracted as a low brightness region 326 (see FIG. 12(e)). The contour 327 of the low brightness region 326 extracted in this manner can then be derived as a line that forms the outer edge of the medicine (see FIG. 12(f)).

On the other hand, the front side image 323 is an image obtained by photographing the medicine on the inspection unit 30 from the front side, and in addition to the medicine, the plate body that forms the inspection unit 30 is photographed in the background. Moreover, as described above, the positional relationship of the regions contained in the backlight image 322 and the front side image 323 is a respectively corresponding relationship. Therefore, in the front side image 323, the region corresponding to the region enclosed by the medicine contour derived using the backlight image 322 is the region that corresponds to the medicine. More specifically, if a contour 327 like that shown in FIG. 12(f) is derived as described above, the region in the front side image 323 that corresponds to the region enclosed by the contour 327 is the region that corresponds to the medicine as shown in FIG. 12(g). Accordingly, the image of the medicine can be cut from the background image and acquired by extracting the region in the front side image 323 using the above-described contour 327 as an indicator.

Here, as described above, if the medicine is opaque (not translucent), the contour of the medicine can be derived with relative ease and accuracy from the backlight image 322. However, if the medicine is translucent, the medicine is not photographed as a shadow in the backlight image 322, and similar to the background portion, the medicine is projected brightly in the photographed image with the light in a transmitted state. Therefore, it is difficult to derive the contour 327 of a translucent medicine based on the difference in contrast in a backlight image 322 (see FIG. 13(b)).

On the other hand, if a medicine is translucent, the chroma saturation in the front side image 323 is clearly different from the region where the medicine is arranged (hereinafter, also referred to as a "medicine arrangement region 328") and the other region (background region 329). More specifically, as shown in FIG. 13(c), if an image pertaining to the chroma component of the front side image 323 (hereinafter, also referred to as the "chroma saturation image") is obtained, the medicine arrangement region 328 can be clearly differentiated from the background region 329. In other words, the brightness is significantly different between the medicine arrangement region 328 and the background region 329, and the medicine arrangement region 328 is brighter than the background region 329. Therefore, processing is implemented on an image (FIG. 13(d)) from which noise has been removed from the chroma saturation image shown in FIG. 13(c) to derive the high brightness region based on brightness (see FIG. 13(e)). As shown in FIG. 13(f), by deriving the contour 330 of the high brightness region obtained in this manner, a state is obtained in which the medicine arrangement region 328 of a translucent medicine can be differentiated from the background region 329. As shown in FIG. 13(g), by applying the contour 330 obtained in this manner to the backlight image, the image of the translucent medicine can be cut and extracted from the background image. The image of a translucent medicine extracted in this manner can then be registered in the master database as a master image for inspection.

Figure 14:
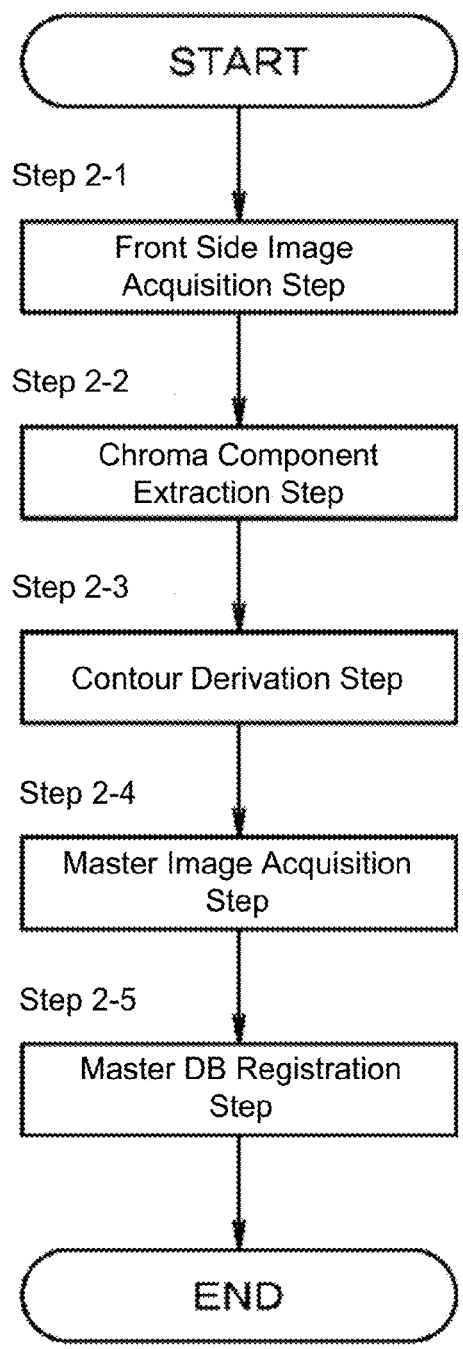
FIG. 14 is a flow chart showing an image processing method that is executed to obtain a master image for inspecting a translucent medicine.

In other words, when a medicine is translucent, a master image for inspection can be obtained by implementing image processing in accordance with the flow chart shown in FIG. 14. More specifically, first a front side image like that shown in FIG. 13(a) is acquired in a front side image acquisition step of Step 2-1. Next, an image for which only the chroma component has been extracted from the front side image (chroma component extracted image) is acquired in the chroma component extraction step of Step 2-2.

When the chroma component extracted image is obtained, image processing to obtain a contour 330 is implemented in a contour 330 derivation step of Step 2-3. In other words, in Step 2-3, first, image processing to extract a region of high brightness (high brightness region) from the chroma component extracted image is implemented (see FIG. 13(e), after which, the outer edge of the high brightness region is derived as the contour 330 (see FIG. 13(f)).

When a contour 330 is derived as described above, a master image is acquired in a master image acquisition step of Step 2-4. In other words, image processing to superimpose the contour 330 obtained in Step 2-3 onto the front side image 323 of FIG. 13(a) is performed. Through this, as shown in FIG. 13(g), the region where the medicine is photographed in the front side image 323 becomes enclosed by a contour 330. The master image can then be obtained by cutting out the region enclosed by the contour 330 in the front side image 323.

When a master image is obtained in Step 2-4 as described above, in Step 2-5, the master image is registered in the master database in a state of being associated with the medicine type and the like. The series of control flow is then completed in this manner.

The present invention is not limited to the above-described embodiments illustrated as a first embodiment and a second embodiment or to the modified examples given for each of the embodiments, and a person skilled in the art could easily understand from learning and from the spirit of the invention that other embodiments can be obtained within a scope that does not depart from the scope of the claims.

REFERENCE SYMBOLS

10: medicine inspection device
60: control device
62: inspection database
64: prescription history database
100: medicine dividing and packaging device
130: medicine supply means
138: manual medicine supply unit
180: medicine packaging means
S: system for individually packaging medicine

What is claimed is:

1. A medicine inspection device for inspecting whether or not a medicine has been divided and packaged according to a prescription in a divided packaging bag formed by dividing and packaging the medicine into single packages based on the prescription using a medicine dividing and packaging device, the medicine inspection device comprising:
    an inspection database in which information regarding medicines necessary for implementing an inspection is accumulated; and
    a control device performing similarity determination by referencing the inspection database and outputting the presence of a medicine similar to a medicine divided and packaged in the divided packaging bag as a determination result;
    wherein, the control device performs similarity determination through a preparation medicine limiting mode, which limits the reference scope of the inspection database to within a scope of medicines registered as medicines to be packaged by the medicine dividing and packaging device.

2. The medicine inspection device according to claim 1, wherein the control device performs similarity determination through an adopted medicine limiting mode, which limits the reference scope of the inspection database to within a scope of medicines registered as medicines to be prepared for dividing and packaging from amongst medicines registered in the inspection database.

3. The medicine inspection device according to claim 1, wherein the control device performs similarity determination through an identical divided and packaged medicine limiting mode, which limits the reference scope of the inspection database to within a scope of medicines contained within a divided packaging bag.

4. The medicine inspection device according to claim 1, wherein the control device performs similarity determination through an identical prescription medicine limiting mode, which limits the reference scope of the inspection database to within a scope of medicines used in prescriptions of a same patient.

5. The medicine inspection device according to claim 1, wherein the control device performs similarity determination through a prescription history limiting mode, which limits the reference scope of the inspection database to within a scope of medicines having a history of being prescribed for the patient corresponding to the divided packaging bag that is the target of inspection.

6. The medicine inspection device according to claim 1, wherein a determination level uniformizing mode, which implements similarity determination using a reference scope of the inspection database as a same scope for all single divided packaging bag groups divided and packaged based on a same prescription, and
- a determination level weighting mode, which dissimilates the reference scope of the inspection database during similarity determination based on when an inspection is performed for a divided packaging bag which forms a portion of the divided packaging bag group and when an inspection is performed for other divided packaging bags, can be selected;
and conditional upon the medicine dividing and packaging device having a manual medicine supply unit capable of dispersing and inserting medicines in single package portions at a time, and capable of supplying single package portions at a time as portions for dividing and packaging,
by selecting the determination level weighting mode,
similarity determination performs the reference scope of the inspection database referenced in the similarity determination regarding a divided packaging bag in which medicines prepared by the manual medicine supply unit are packaged is a broader scope than the reference scope of the inspection database referenced in a similarity determination regarding other divided packaging bags.

7. The medicine inspection device according to claim 1, wherein a determination level uniformizing mode, which implements similarity determination using a reference scope of the inspection database as a same scope for all single divided packaging bag groups divided and packaged based on a same prescription, and
- a determination level weighting mode, which dissimilates the reference scope of the inspection database during similarity determination based on when an inspection is performed for a divided packaging bag which forms a portion of the divided packaging bag group and when an inspection is performed for other divided packaging bags, can be selected;
and by selecting the determination level weighting mode,
similarity determination performs the reference scope of the inspection database referenced in the similarity determination regarding a divided packaging bag in which medicines registered as medicines requiring caution from amongst medicines registered in the inspection database is a broader scope than the reference scope of the inspection database referenced in a similarity determination regarding other divided packaging bags.

8. The medicine inspection device according to claim 1, wherein a medicine type comparison inspection, which implements a comparison including a similarity determination regarding whether or not the medicine type of the medicine divided and packaged in the divided packaging bag matches the prescription, and a quantity comparison inspection, which determines whether or not the quantity of the medicine is in accordance with the prescription, are performed; and
- a full comparison mode, which implements both the medicine type comparison inspection and the quantity comparison inspection, and
- a quantity comparison limited mode, which implements the quantity comparison inspection without implementing the medicine type comparison inspection, can be selectively implemented.

9. The medicine inspection device according to claim 1, wherein an inspection is performed to determine whether or not a medicine that is divided and packaged matches a prescription based on color information obtained from a photographed image of the medicine that is the target of inspection;
- the medicine inspection device comprises a database in which color information of medicines is recorded, and an inspection is performed to determine whether or not a medicine targeted for inspection is a medicine compared in the database by comparing color information of the medicine obtained from the photographed imaged and color information of each medicine registered in the database;
- regarding long medicines having a long shape in a prescribed direction and for which the color is different with a center part in the longitudinal direction as a boundary, color information for one side of the boundary and color information for the other side of the boundary are recorded respectively as master data (Mα, Mβ) in the database;
- color information for a region on one side (RA) of a long medicine and color information for a region on the other side (RB) thereof with a center part in the longitudinal direction as a boundary are respectively derived from an image of a long medicine in a photographed image; and
- if a combination of the color information (RA, RB) matches a combination of the master data (Mα, Mβ) for a long medicine compared in the database, a determination is made that the medicine thereof is the long medicine to which it was compared.

10. A medicine inspection device for inspecting whether or not a medicine has been divided and packaged according to a prescription in a divided packaging bag formed by dividing and packaging the medicine into single packages based on the prescription using a medicine dividing and packaging device, the medicine inspection device comprising:
- a conveying means for conveying a continuous divided packaging bag body having divided packaging bags formed continuously via a boundary;
- an inspection unit at which divided packaging bags that are the target of inspection are arranged;
- a photographing device for photographing a divided packaging bag arranged at the inspection unit through conveyance by the conveying means;
- an inspection database in which information regarding medicines including master images pertaining to the exterior shapes of medicines is accumulated; and
- a control device performing image matching processing to match a master image registered in the inspection database and an image obtained by the photographing device, medicine inspection processing to inspect whether or not a medicine has been packaged in accordance with a prescription in a divided packaging bag, and supply control to convey and supply the continuous divided packaging bag body by the conveying means;

wherein a divided packaging bag targeted for inspection is supplied to the inspection unit by the supply control, and if both a boundary on the upstream side and a boundary on the downstream side in the conveyance direction with respect to the divided packaging bag that has arrived at the inspection unit are contained in an image photographed by the photographing device, the control device determines that the divided packaging bag that is the target for inspection has been positioned with good precision with respect to the inspection unit; and if only one of either the boundary on the upstream side or the boundary on the downstream side in the conveyance direction with respect to the divided packaging bag that has arrived at the inspection unit is contained in the image, the control device determines that the divided packaging bag is in a state of being positionally deviated with respect to the inspection unit.

11. The medicine inspection device according to claim 10, wherein if only the boundary on the upstream side in the conveyance direction with respect to the divided packaging bag that has arrived at the inspection unit is contained in the image, the control device determines that the divided packaging bag is in a state of being positionally deviated at the downstream side with respect to the inspection unit; and if only the boundary on the downstream side in the conveyance direction with respect to the divided packaging bag that has arrived at the inspection unit is contained in the image, the control device determines that the divided packaging bag is in a state of being positionally deviated at the upstream side with respect to the inspection unit.

12. A medicine inspection device for inspecting whether or not a medicine has been divided and packaged according to a prescription in a divided packaging bag formed by dividing and packaging the medicine into single packages based on the prescription using a medicine dividing and packaging device, the medicine inspection device comprising:

an inspection unit at which divided packaging bags that are the target of inspection are arranged;

a photographing device for photographing a divided packaging bag arranged at the inspection unit through conveyance by the conveying means;

an inspection database in which information regarding medicines including master images pertaining to the exterior shapes of medicines is accumulated; and a control device performing image matching processing to match a master image registered in the inspection database and an image obtained by the photographing device, and of implementing medicine inspection processing to inspect whether or not a medicine has been packaged in accordance with a prescription in a divided packaging bag; and performing a master image acquisition operation to acquire the master image pertaining to the medicine based on images of medicines acquired by the photographing device;

wherein with the master image acquisition operation, a step of acquiring a front side image obtained by using the photographing device to photograph a divided packaging bag arranged at the inspection unit and a medicine arranged at the inspection unit;

a step of acquiring an image for which the chroma component of the front side image has been extracted;

a step of deriving a high brightness region which has a higher level of brightness than a prescribed brightness in the image for which the chroma component has been extracted;

a step of deriving a contour of the high brightness region; and a step of acquiring as a master image an image within a region corresponding to a region enclosed by the contour in the front side image can be executed.

13. A system for individually packaging medicine, comprising:

a medicine inspection device; and a medicine dividing and packaging device performing dividing and packaging a medicine into divided packaging bags in single package portions in accordance with a prescription;

wherein medicines that have been divided and packaged at the medicine dividing and packaging device can be inspected by the medicine inspection device;

the medicine inspection device is for inspecting whether or not the medicine has been divided and packaged according to the prescription in the divided packaging bag formed by dividing and packaging the medicine into single packages based on the prescription using the medicine dividing and packaging device; and the medicine inspection device comprises: an inspection database in which information regarding medicines necessary for implementing an inspection is accumulated; and a control device performing similarity determination by referencing the inspection database and outputting the presence of a medicine similar to a medicine divided and packaged in the divided packaging bag as a determination result wherein, the control device performs similarity determination through a preparation medicine limiting mode, which limits the reference scope of the inspection database to within a scope of medicines registered as medicine s to be packaged by the medicine dividing and packaging device.

* * * * *